(12) United States Patent
Mostafa et al.

(10) Patent No.: US 11,027,270 B1
(45) Date of Patent: Jun. 8, 2021

(54) METHOD OF PERFORMING COUPLING REACTIONS

(71) Applicant: KING ABDULAZIZ UNIVERSITY, Jeddah (SA)

(72) Inventors: Mohamed Mokhtar Mohamed Mostafa, Jeddah (SA); Ghalia Saeed Alzhrani, Jeddah (SA); Elham Shafik Aazam, Jeddah (SA); Tamer Said Sayed Saleh, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/146,542

(22) Filed: Jan. 12, 2021

(51) Int. Cl.
| | |
|---|---|
| *C07C 2/84* | (2006.01) |
| *C07C 15/50* | (2006.01) |
| *B01J 23/755* | (2006.01) |
| *B01J 37/03* | (2006.01) |
| *B01J 35/00* | (2006.01) |
| *B01J 37/02* | (2006.01) |
| *B01J 29/08* | (2006.01) |
| *C07C 41/30* | (2006.01) |

(52) U.S. Cl.
CPC ........... *B01J 37/031* (2013.01); *B01J 23/755* (2013.01); *B01J 29/084* (2013.01); *B01J 35/0006* (2013.01); *B01J 37/0215* (2013.01); *C07C 2/84* (2013.01); *C07C 15/50* (2013.01); *C07C 41/30* (2013.01); *C07C 2529/14* (2013.01)

(58) Field of Classification Search
None
See application file for complete search history.

(56) References Cited

U.S. PATENT DOCUMENTS

| | | | | |
|---|---|---|---|---|
| 2004/0192542 A1* | 9/2004 | Choudary | ............ | B01J 31/0295 502/159 |
| 2017/0297009 A1* | 10/2017 | Suriye | ...................... | B01J 37/04 |

OTHER PUBLICATIONS

Mokhtar et al., Synergistic Effect of NiLDH@YZ Hybrid and Mechanochemical Agitation of Glaser Homocoupling Reaction, Chemistry—A European Journal, Apr. 13, 2021, pp. 1-12. (Year: 2021).*

(Continued)

*Primary Examiner* — Philip Y Louie
(74) *Attorney, Agent, or Firm* — W & C IP

(57) ABSTRACT

A method of preparing an amalgamated transition metal layered double hydroxide (LDH)@Y-zeolite hybrid catalyst is provided. The method includes combining a transition metal with aluminum nitrate and precipitating using an alkali under ultrasound irradiation and an inert atmosphere to form a transition metal-containing LDH catalyst. A Y-zeolite is pretreated by an ion exchange process utilizing ammonia prior to calcination at temperature (250-1000° C.) under an inert atmosphere to form an H—Y-zeolite. Followed by refluxing the transition metal-containing LDH catalyst together with the H—Y-zeolite at 50° C. for a predetermined time to form a precipitate. The precipitate is filtering and washing with distilled water to obtain the amalgamated transitional metal LDH@Y-zeolite hybrid catalyst. The disclosure also relates to a method for performing a terminal alkyne dehydrogenation coupling reaction involving a synergetic effect of a bill mill and an amalgamated transition metal layered double hydroxide (LDH)@Y-zeolite hybrid catalyst.

13 Claims, 16 Drawing Sheets

(56) References Cited

OTHER PUBLICATIONS

Kuhn et al., "Copper-Zeolites as Catalysts for the Coupling of Terminal Alkynes: An Efficient Synthesis of Diynes", Eur. J. Org. Chem., 2009, p. 423-429. (Year: 2009).*

Liu et al., "Enaminone ligand-assisted homo- and cross-coupling of terminal alkynes under mild conditions", Tetrahedron Letters 54, 2013, p. 3953-3955. (Year: 2013).*

Chen et al., "Core-shell zeolite@ aqueous miscible organic-layered double hydroxides", The Royal Society of Chemistry, 2016, p. 1457-1461. (Year: 2016).*

Li et al., "Microporous Zeolite@Vertically Aligned Mg—Al Layered Double Hydroxide Core@Shell Structures with Improved Hydrophobicity and Toluene Adsorption Capacity under Wet Conditions", ACS Applied Materials & Interfaces, 2018, p. 3434-34839. (Year: 2018).*

Namitharan et al., "Nickel-Catalyzed Solvent-Free Three-Component Coupling of Aldehyde, Alkyne and Amine", Eur. J. Org. Chem., 2010, p. 411-415. (Year: 2010).*

\* cited by examiner

METHOD OF PERFORMING COUPLING REACTIONS

TECHNICAL FIELD

The present disclosure relates to preparation of a transition metal layered double hydroxide (LDH) hybrid catalyst. More specifically, the present disclosure relates to use of a transitional metal LDH@Y-zeolite hybrid catalyst for coupling reactions.

BACKGROUND

Dehydrogenative coupling is a chemical process where a new chemical bond is formed either by hydrogen evolution or by formal removal of hydrogen from a substrate. Despite, selectively breaking a C—H/X—H bond in a pool of similar bonds and making a desired C—C/C—X/X—X bond are associated with prominent challenges. Glaser reaction, homocoupling of terminal alkyne proceeds in presence of copper salts and air, is very important for formation of precursor for products in material science, molecular electronics, for the synthesis of polymers, supramolecular materials, and drug manufacturing. Although, several strategies have been devised to achieve dehydrogenative coupling, most of the strategies are accompanied with various drawbacks. Most of the strategies are complex, lengthy, time consuming and depend on several variables such as pH, temperature, and crystallization. In addition, the existing strategies create numerous by-products detrimental to the environment.

Basic requirement to achieve dehydrogenative process is that the substrate should possess either a directing group or liable C—H bond. One of the ways is choosing a suitable nickel salts which is still quite challenging, it is recommended to generate Ni (0) with reasonable ligand that could possibly minimize the undesired byproducts. However, even in this strategy, there are several drawbacks including lack of sustainability, high risk of organovolatile solvent, long reaction time and low yield. Considering the importance of the coupling reaction for several industries, there is a dire need to provide a simple, safe and environmentally friendly catalyst. The catalyst should be easy to prepare and work efficiently under mild conditions with minimal detrimental impact on the environment. The catalyst should also have high reusability as well as high reliability for smooth conducting of coupling reactions.

BRIEF DESCRIPTION OF THE DRAWINGS

The drawings described below are for illustration purposes only and are not intended to limit the scope of the present disclosure in any way.

SUMMARY

Figure 1:
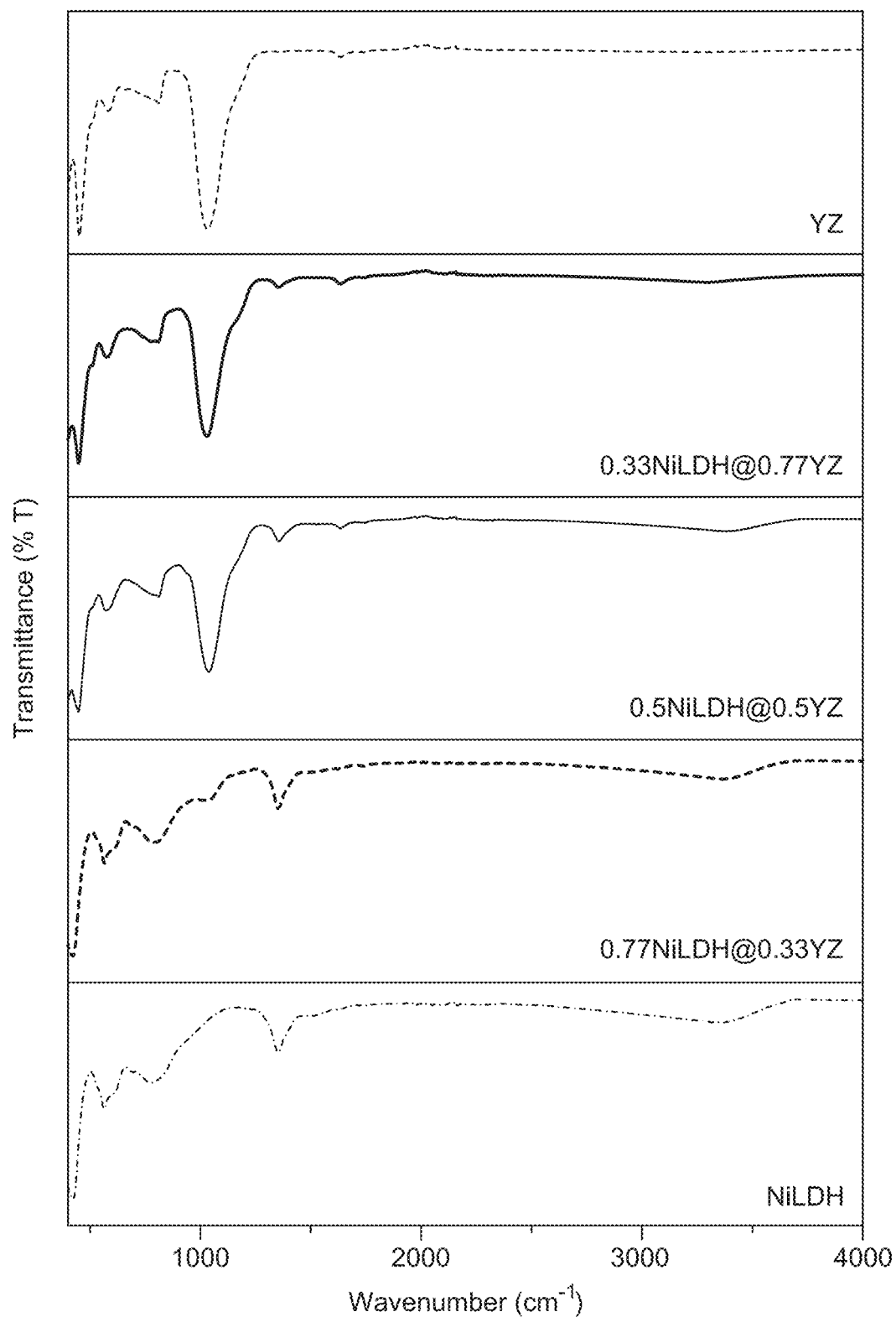
FIG. 1 shows Fourier-transform infrared spectroscopy (FTIR) spectrum of synthesized NiLDH, (Y-zeolite) YZ and NiLDH, YZ hybrids.

The present disclosure relates to a method of preparing an amalgamated transition metal layered double hydroxide (LDH)@Y-zeolite hybrid catalyst. The disclosure also relates to a method for performing a terminal alkyne dehydrogenation coupling reaction involving a synergetic effect of a bill mill and an amalgamated transition metal layered double hydroxide (LDH)@Y-zeolite hybrid catalyst.

In one aspect, the present disclosure includes the method of preparing the amalgamated hybrid catalyst by combining a transition metal with aluminum nitrate and precipitating using an alkali under ultrasound irradiation and an inert atmosphere to form a transition metal-containing LDH catalyst. The method includes pretreating a Y-zeolite by an ion exchange process by ammonia before calcination at a temperature between 250 to 1000° C. under an inert atmosphere to form an H—Y-zeolite. The H—Y-zeolite is refluxed with the transition metal-containing LDH catalyst together at 50° C. for a predetermined time to form a precipitate. The precipitate is filtered and washed with distilled water to obtain the amalgamated transitional metal LDH@Y-zeolite hybrid catalyst. In some embodiments, the method of preparing the amalgamated hybrid catalyst further includes coating the transitional metal LDH catalyst onto the surface of the Y-zeolite.

In some embodiments, the transitional metal is nickel, cobalt, molybdenum, vanadium, copper, palladium, manganese, and transitional metal ions. In certain embodiments, the transitional metal is nickel and the transitional metal LDH@Y-zeolite hybrid catalyst is a hybrid nickel layered double hydroxide/Y-zeolite catalyst. In other embodiments, the amalgamated transitional metal LDH@Y-zeolite hybrid catalyst is amphoteric. The disclosure incudes a method of using the amalgamated transitional metal LDH@Y-zeolite hybrid catalyst in preparation of pharmaceuticals, nanotechnology products, semiconductors, pollution sensors, and organic compounds.

In another aspect, the present disclosure relates to the method for performing a terminal alkyne dehydrogenation coupling reaction. The method includes combining a transitional metal LDH@Y-zeolite hybrid catalyst to a terminal alkyne and pyrrolidine to form a mixture and transferring a portion of the mixture into a ball mill. A mechanochemical agitation of the portion of the mixture is performed in the ball mill for a first predetermined time to form a reaction mixture. The reaction mixture is oxidized for a second predetermined time. A filtrate of the oxidized reaction mixture is obtained followed by concentrating the filtrate in a vacuum under reduced pressure. The concentrated filtrate is purified by chromatography to obtain a purified end product of the terminal alkyne dehydrogenation coupling reaction. In some embodiment, the purified end product yield is more than or equal to 80%. The embodiments of the present method also include using the amalgamated transitional metal LDH@Y-zeolite hybrid catalyst for at least 4 cycles. In certain embodiments, the transitional metal LDH@Y-zeolite hybrid catalyst is a NiLDH@YZ hybrid catalyst. In one embodiment, the NiLDH@YZ hybrid catalyst is a 0.5NiLDH@0.5YZ hybrid catalyst. In some other embodiments, the method for performing a terminal alkyne dehydrogenation coupling reaction further includes oxidizing the reaction mixture using an oxidant, where the oxidant is air. In yet another embodiment, the method includes filtering the oxidized reaction mixture by using ethyl acetate. In some embodiments, the method includes sonicating the reaction mixture for less than or equal to 5 minutes. In other embodiments, the coupling reaction is completed is less than or equal to 60 minutes.

In some embodiments, the transitional metal is nickel and the transitional metal LDH@Y-zeolite hybrid catalyst is a hybrid nickel layered double hydroxide/Y-zeolite catalyst. In some embodiments, the amalgamated transitional metal LDH@Y-zeolite hybrid catalyst is amphoteric. In certain embodiments, the method of preparing the amalgamated hybrid catalyst is solvent-free. In other embodiments, the coupling reaction is a homocoupling reaction. In one embodiment, the homocoupling reaction is a Glaser homo-coupling reaction. In another embodiment, the coupling reaction is a cross-coupling reaction.

The foregoing as well as other features and advantages of the present disclosure will be more fully understood from the following description, examples, and claims.

DETAILED DESCRIPTION

Reference will now be made in detail to specific embodiments or features, examples of which are illustrated in the accompanying drawings. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention. Any method steps, and processes described herein are not to be construed as necessarily requiring their performance in the particular order discussed or illustrated, unless specifically identified as an order of performance. It is also to be understood that additional or alternative steps may be employed, unless otherwise indicated.

The present disclosure discloses a method of preparing an amalgamated transition metal layered double hydroxide (LDH)@Y-zeolite hybrid catalyst. The method includes combining a transition metal with aluminum nitrate and precipitating using an alkali under ultrasound irradiation and an inert atmosphere to form a transition metal-containing LDH catalyst. The method further includes pretreating a Y-zeolite by an ion exchange process utilizing ammonia prior to calcination at a temperature between 250 to 1000° C. under an inert atmosphere to form an H—Y-zeolite and refluxing the transition metal-containing LDH catalyst together with the H—Y-zeolite at 50° C. for a predetermined time to form a precipitate. The refluxing step is followed by filtering the precipitate and washing with distilled water to obtain the amalgamated transitional metal LDH@Y-zeolite hybrid catalyst.

The present disclosure also discloses a method of performing a terminal alkyne dehydrogenation coupling reaction. The method includes combining an amalgamated transitional metal LDH@Y-zeolite hybrid catalyst to a terminal alkyne and pyrrolidine to form a mixture and transferring a portion of the mixture into a ball mill. The method further includes performing a mechanochemical agitation of the portion of the mixture in the ball mill for a first predetermined time to form a reaction mixture. This is followed by oxidizing the reaction mixture for a second predetermined time and filtering the oxidized reaction mixture to obtain a filtrate. The method includes concentrating the filtrate in a vacuum under reduced pressure and purifying the concentrated filtrate using chromatography to obtain a purified end product of the terminal alkyne dehydrogenation coupling reaction.

As used herein, "coupling reaction" refers to any reaction wherein two chemical species or fragments are combined together with the aid of a metal catalyst. Coupling reaction includes homo-coupling or any known forms of homo coupling, or cross coupling reactions.

As used herein, "homo-coupling reaction" refers to any coupling reaction involving combination of identical chemical species or fragments.

As used herein, "Glaser homo-coupling reaction" refers to any synthesis of symmetric or cyclic bisacetylenes via a coupling reaction of terminal alkynes.

As used herein, "transitional metal" include all d-block, the f-block lanthanide and actinide series of the periodic table in any known forms.

As used herein, "LDH" or "layered double hydroxide" refers to layered structures represented by the formula $[A_cB\ Z\ A_cB]_n$, where c represents layers of metal cations, A and B are layers of hydroxide ($HO^-$) anions, and Z are layers of other anions and neutral molecules.

As used herein, "chromatography" refers to column chromatography, thin layer chromatography (TLC), planar chromatography, gas chromatography, liquid chromatography, supercritical fluid chromatography, ion exchange chromatography, size-exclusion chromatography, and expanded bed adsorption chromatographic separation or any such method of separation that follows the principle of chromatography.

As used herein, "terminal alkyne dehydrogenation" refers to chemical process where a new chemical bond is formed either by hydrogen evolution or by formal removal of hydrogen from a substrate.

As used herein, "hybrid catalyst" or "catalyst" or "transition metal layered double hydroxide (LDH)@Y-zeolite hybrid catalyst" or "LDH catalyst" or "hybrid LDH catalyst" or "amalgamated transitional metal LDH@Y-zeolite hybrid catalyst" are used synonymously, unless specified otherwise.

As used herein, "amount" refers to the level or concentration of one or more reactants, catalysts, present in a reaction mixture.

The use of the singular herein includes the plural (and vice versa) unless specifically stated otherwise.

The use of the terms "include," "includes", "including," "have," "has," or "having," "comprise," "comprises," "comprising" or the like should be generally understood as open-ended and non-limiting unless specifically stated otherwise.

It is understood that the order of steps or order for performing certain actions can be changed so long as the intended result is obtained. Moreover, two or more steps or actions may be conducted simultaneously.

As used herein, the term "about" or "between" refers to a ±20% to ±10% variation from the nominal value unless otherwise indicated.

The present disclosure includes the method of preparing the amalgamated transition metal layered double hydroxide (LDH)@Y-zeolite hybrid catalyst. In some embodiments, the transitional metal is selected from a group comprising nickel, cobalt, molybdenum, vanadium, copper, palladium, manganese, and ions. In one embodiment the transition metal is nickel and the amalgamated transitional metal LDH@Y-zeolite hybrid catalyst is a hybrid nickel layered double hydroxide/Y-zeolite catalyst. In some embodiments, the amalgamated transitional metal LDH@Y-zeolite hybrid catalyst is amphoteric displaying both acid and basic behavior.

The method of preparing an amalgamated transition metal layered double hydroxide (LDH)@Y-zeolite hybrid catalyst includes coating the transitional metal LDH catalyst onto the surface of the Y-zeolite. In certain embodiments, the method includes coating nickel LDH onto the surface of the Y-zeolite.

The present disclosure further relates to a method of using the hybrid transitional metal layered double hydroxide/Y-zeolite catalyst in preparation of products including pharmaceuticals, nanotechnology products, semiconductors, pollution sensors, and organic compounds. In some embodiments, the hybrid transitional metal layered double hydroxide/Y-zeolite catalyst is used for the greener and environmentally friendly characteristics of the hybrid catalyst.

The disclosure also includes the method for performing the terminal alkyne dehydrogenation coupling reaction with high end product yield. In some embodiments, the yield of the purified end product is more than or equal to 80%. In an embodiment, the yield of the purified end product of the terminal alkyne dehydrogenation coupling reaction using the method of the present disclosure is equal to 83%. In some embodiments, the method for performing the terminal alkyne dehydrogenation coupling reaction further includes filtering the oxidized reaction mixture using ethyl acetate. In one embodiment, the hybrid catalyst is removed after the completion of the reaction by filtration, washed with hot ethyl acetate and dried under vacuum conditions. In certain embodiments, the method further includes sonicating the reaction mixture for less than or equal to 5 minutes. One of the advantages of the methods of present disclosure includes a very efficient reaction rate. In some embodiments, the coupling reaction is completed in less than or equal to 60 minutes.

The methods of the present disclosure are simple, cost-effective and reduce pollution. The present disclosure includes the method for performing the terminal alkyne dehydrogenation coupling reaction where the reaction is a solvent-free reaction. The methods also include using the amalgamated transitional metal LDH@Y-zeolite hybrid catalyst for multiple times. In some embodiments, the methods include using the amalgamated transitional metal LDH@Y-zeolite hybrid catalyst for at least 4 cycles.

The present disclosure also includes the method for performing the terminal alkyne dehydrogenation coupling reaction where the reaction mixture is oxidized. In various embodiments, the method includes using an oxidant. In one embodiment, the oxidant is air. In another embodiment, the method includes oxidizing the reaction mixture in pure oxygen. In some embodiments, the oxidation step includes oxidizing the reaction mixture in a vacuum with pure oxygen.

The disclosure includes the method for performing the terminal alkyne dehydrogenation coupling reaction. Thus, in various embodiments, the coupling reaction is a homocoupling reaction involving combination of identical chemical species or fragments. In some embodiments, the homocoupling reaction is a Glaser homocoupling including synthesis of symmetric or cyclic bisacetylenes via the coupling reaction of terminal alkynes. In some embodiments, the coupling reaction is a cross-coupling reaction. The disclosure includes performing the cross-coupling reaction where the cross-coupling is a Kumada coupling, Heck reaction, Sonogashira coupling, Negishi coupling, Stille cross coupling, Suzuki reaction, Hiyama coupling, Buchwald-Hartwig reaction, Fukuyama coupling, or a Liebeskind-Srogl coupling. In an embodiment, the cross-coupling reaction is a Suzuki reaction.

The methods of present disclosure include the method for performing the terminal alkyne dehydrogenation coupling reaction by combining the transitional metal LDH@Y-zeolite hybrid catalyst to the terminal alkyne and pyrrolidine to form the mixture. In some embodiments, the transitional metal LDH@Y-zeolite hybrid catalyst is a NiLDH@YZ hybrid catalyst. The hydroid catalyst of the present disclosure includes preparing the catalyst at different concentrations of the LDH and the Y-zeolite. Thus, the hybrid catalysts include a 0.77NiLDH@0.33YZ, a 0.5NiLDH@0.5YZ and a 0.33NiLDH@0.77YZ. In some embodiments, the hybrid catalyst used to perform the Glaser coupling reaction with the bill mill is the NiLDH@YZ hybrid catalyst. In one embodiment, the NiLDH@YZ hybrid catalyst used to perform the Glaser coupling reaction with the bill mill is the 0.5NiLDH@0.5YZ catalyst. The 0.5NiLDH@0.5YZ catalyst has higher total number of basic sites, which shows the stronger dispersion of NiLDH in the YZ cavities and therefore provide more efficient reaction yields according to the methods of present disclosure.

The method for performing the terminal alkyne dehydrogenation coupling reaction according to the present disclosure also includes the mechanochemical agitation of the portion of the mixture in the ball mill for the first predetermined time to form a reaction mixture. The ball mill provides milder reaction conditions, increased surface area and surface energy. The increased surface energy in the mechanochemical mode is an outcome of alteration in the structure, chemical composition and chemical reactivity which is a resultant of milling. The frequency at which the ball milling is conducted also impacts the reaction product. Thus, in some embodiments of the present disclosure, the frequency for the reaction ranges between 10 to 40 Hz. In a specific embodiment, the frequency of ball mill is 30 Hz. In certain embodiments, the mechanochemical agitation of the reaction mixture in the ball milling step also includes the NiLDH@YZ catalysts into a stainless steel jar fitted with one or more stainless steel balls. Further, the step includes locking the jar and milling at different frequencies. In one embodiment, the progress of the reaction is monitored every 15 minutes by using thin layer chromatography (TLC). The milling process is repeated where necessary until the reaction is complete followed by opening the milling jar to ambient air atmosphere for 60 minutes. In some embodiments, the mechanochemical treatment of the hybrid catalyst changes the microstructure, morphology, induce phase transition and increase the catalytic performance Thus, the synergetic effect of the hybrid catalyst and ball mill reduces the reaction time and provides a higher end product yield.

The method also includes oxidizing the reaction mixture for the predetermined time followed by filtering the oxidized reaction mixture to obtain the filtrate. The concentration of the oxidized reaction mixture increased in the vacuum under reduced pressure. In some embodiments, the predetermined time for oxidation is between 10 to 60 minutes. In one embodiment, the reaction mixture is allowed to oxidize in air for 60 minutes. The method further includes purifying the concentrated filtrate using chromatography to obtain the purified end product of the terminal alkyne dehydrogenation coupling reaction. In an embodiment, the concentrated filtrate is purified by using column chromatography. In another embodiment, the chromatography is thin layer chromatography. In one example, the method includes concentrating the filtrate in the vacuum under reduced pressure and purifying by column chromatography using n-hexane/ethyl acetate mixtures.

The present disclosure further includes the catalytic activity of NiLDH@YZ hybrids on the Glaser homo-coupling reaction in the ball mill. Thus, in an example, the prepared Ni-containing catalysts are used in the transformation of the terminal alkyne 1 into the corresponding derivative. In some embodiments, the corresponding derivatives include 1,4-buta-1,3-diyne, 1,4-Bis(p-tolyl)buta-1,3-diyne, and 1,4-Bis(p-methoxyphenyl)buta-1,3-diyne. In various embodiments of the present disclosure, the hybrid catalyst is amphoteric displaying unique bifunctional acid-base properties. In one embodiment, unique bifunctional acid-base properties provide a superior catalytic effect in the Glaser carbon-carbon homocoupling reaction.

While most of the methods proposed known require utilizing complex operation and are lengthy and time consuming, the methods of the present disclosure are advantageous in providing the results within 60 minutes as a one pot synthesis.

Experimental Results
Catalyst Characterization

FIG. 1 shows FTIR spectrum of synthesized NiLDH, YZ and NiLDH, YZ hybrids, pure NiLDH sample shows absorption bands at 1353 $cm^{-1}$ due to the interlayer carbonate stretching vibration. The peak around 813 $cm^{-1}$ stands for covalent carbonate stretching vibrations. The bands at 614 and 563 $cm^{-1}$ are due to the Al—O stretching, while the peak at 427 $cm^{-1}$ is due to Ni—O bond [Jitianu, M., et al., *Thermal behaviour of hydrotalcite-like compounds: study of the resulting oxidic forms. International Journal of Inorganic Materials,* 2000; (2(2): p. 287-300)], [Mokhtar, M., T. S. Saleh, and S. N. Basahel, *Mg—Al hydrotalcites as efficient catalysts for aza-Michael addition reaction: A green protocol. Journal of Molecular Catalysis A: Chemical,* 2012; (353-354: p. 122-131)]; [Narasimharao, K., et al., *Microwave assisted efficient protocol for the classic Ullmann homocoupling reaction using Cu—Mg—Al hydrotalcite catalysts. Journal of Molecular Catalysis A: Chemical,* 2013; (379: p. 152-162)]. IR spectrum of pure YZ displayed the absorption band at around 1633 $cm^{-1}$, assigned as weak bending vibrations of OH groups and $H_2O$ molecules. Some IR absorption bands in the range of 1360-450 $cm^{-1}$ for YZ signifies the characteristic framework vibrations (T-O-T unit, where T represents $SiO_4$ or $AlO_4$ tetrahedron species). The broad band around 1032 $cm^{-1}$ is characteristic of Si—O—Si stretching vibration originating from the mesoporous silica present in the YZ [Ya'aini, N., N. A. S. Amin, and S. Endud, *Characterization and performance of hybrid catalysts for levulinic acid production from glucose. Microporous and Mesoporous Materials,* 2013; (171: p. 14-23)]. In the IR spectrum of NiLDH@YZ hybrids, bands at 1032 $cm^{-1}$ (Si—O—Si unit of YZ) and 1353 $cm^{-1}$ (interlayered carbonates of NiLDH) were retained with different intensities. Intensity of both the bands depend on percentage of YZ and NiLDH content in the particular hybrid, which confirms the formation of resultant hybrids.

Figure 2:
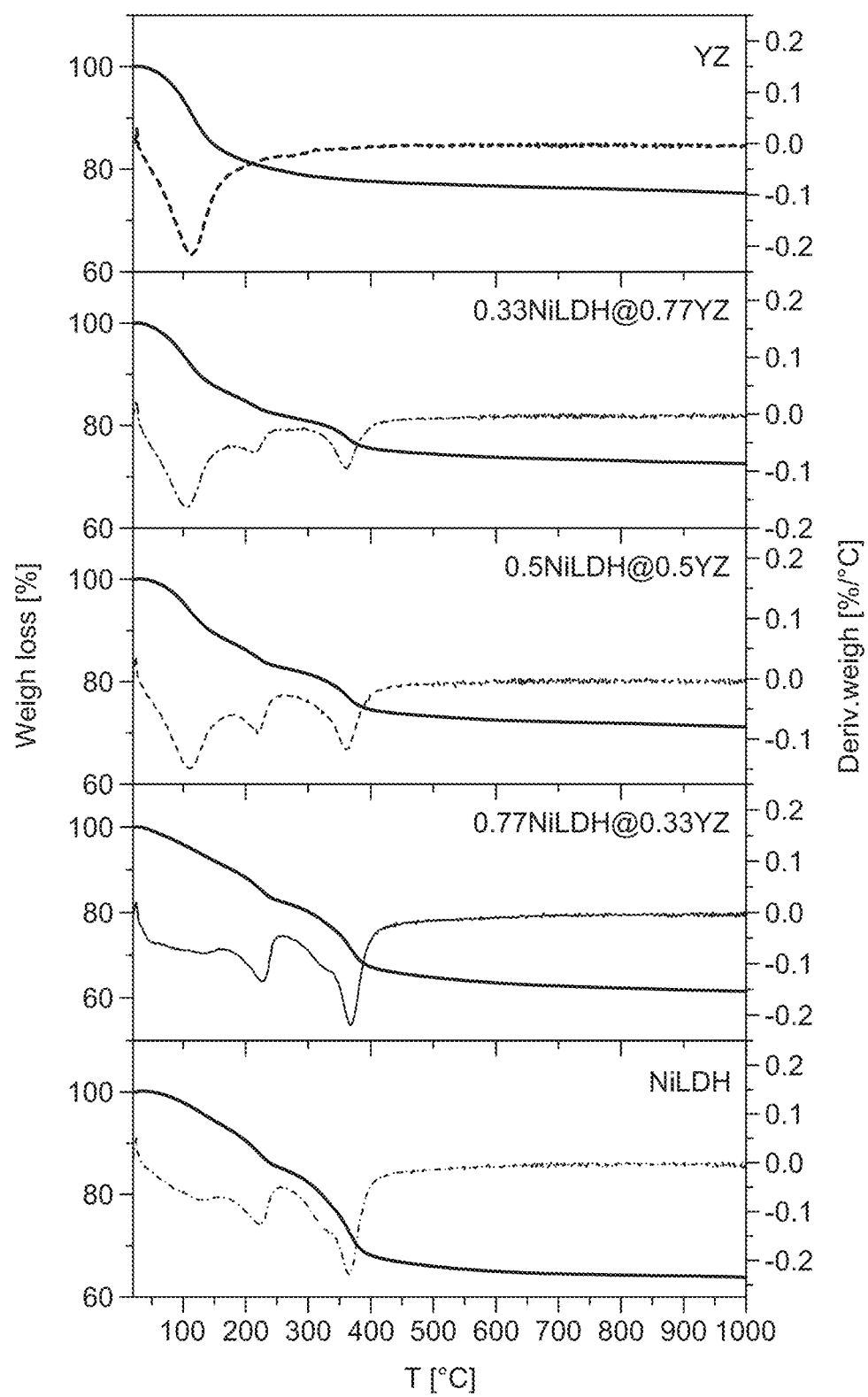
FIG. 2 shows thermograms of YZ, NiLDH and NiLDH@YZ hybrids.

FIG. 2 shows thermograms of YZ, NiLDH and NiLDH@YZ hybrids about the thermal behavior of each material. The thermogram of YZ shows one stage of weight loss (100-120° C.) due to desorption of physisorbed water molecules from the YZ surface [Ya'aini, N., N. A. S. Amin, and S. Endud, *Characterization and performance of hybrid catalysts for levulinic acid production from glucose. Microporous and Mesoporous Materials,* 2013; (171: p. 14-23)]. The thermograms of NiLDH and NiLDH@YZ hybrids show three stages of different weight losses. First stage of weight loss (100-130° C.) represents water desorption from the surface as well as a dehydration step. The second stage of weight loss (210-230° C.) due to the loss of interlayer water molecules and hydroxyl ions [Mokhtar, M., et al., *Thermal decomposition, gas phase hydration and liquid phase reconstruction in the system Mg/Al hydrotalcite/mixed oxide: A comparative study. Applied Clay Science,* 2010; (50(2): p. 176-181)]. The third stage of weight loss which takes place in the range of 350-370° C., due to the decarboxylation of carbonate anions present in the interlayer gallery of NiLDH leading to the formation of metal oxides [Mokhtar, M., et al., *Thermal decomposition, gas phase hydration and liquid phase reconstruction in the system Mg/Al hydrotalcite/mixed oxide: A comparative study. Applied Clay Science,* 2010; (50(2): p. 176-181)]. From the third stage, the amount of $CO_2$ in NiLDH and NiLDH@YZ hybrids have been calculated. The pure zeolite sample YZ did not show evolution of carbon dioxide gas, while the amount of $CO_2$ gas calculated from the third stage in the thermograms was 1.57, 1.95, 3.55, 3.69 mmol $g^{-1}$ for 0.33NiLDH@0.77YZ, 0.5NiLDH@0.5YZ, 0.77NiLDH@0.33YZ and NiLDH samples, respectively. The calculated values match the layered double hydroxides content in each hybrid, and elevated monotonically with the increase in the NiLDH content.

Figure 3:
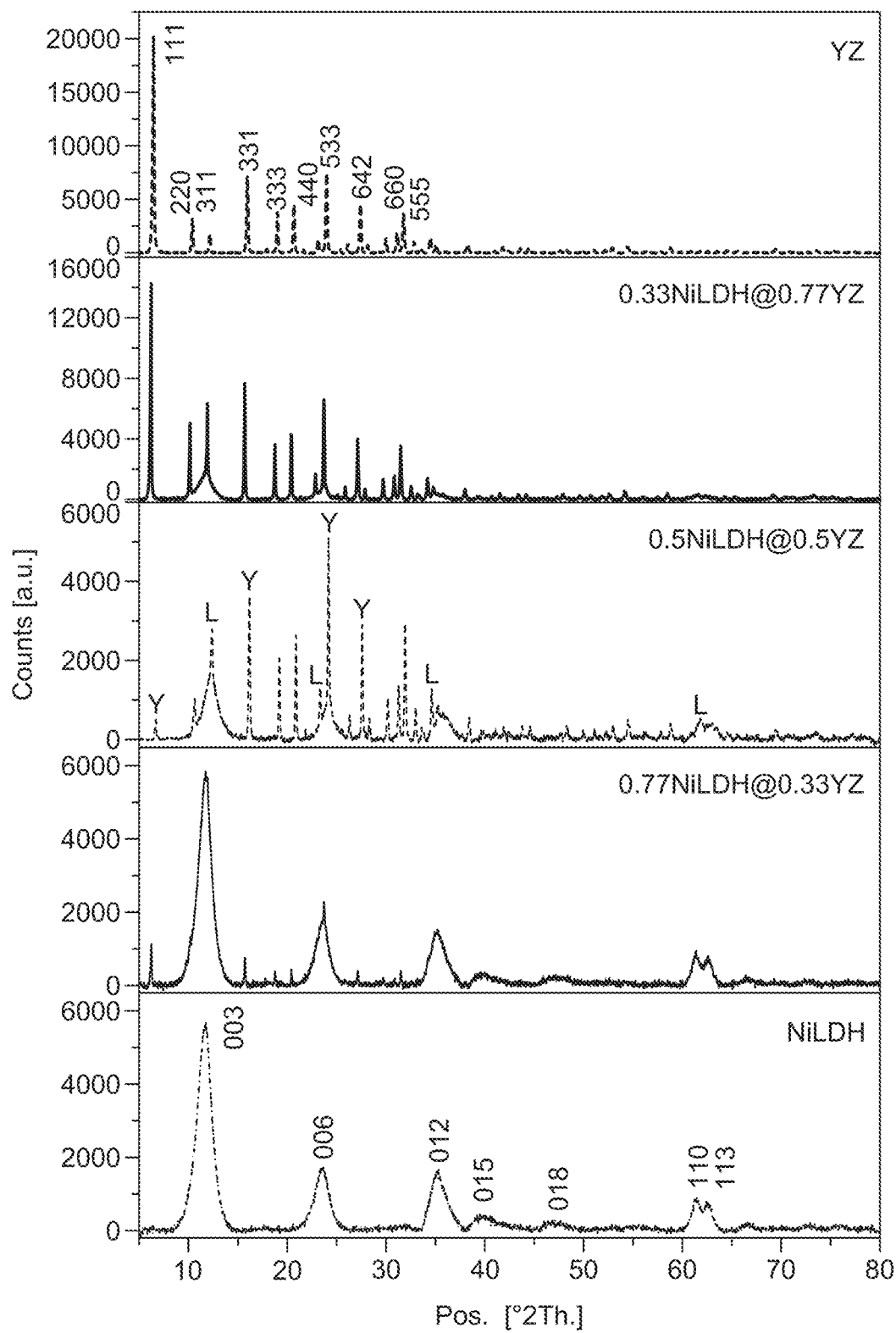
FIG. 3 shows X-ray diffraction (XRD) patterns of NiLDH, YZ and NiLDH, YZ hybrids.

FIG. 3 shows X-ray diffraction (XRD) patterns of NiLDH, YZ and NiLDH, YZ hybrids. The characteristic peak of LDH is at low value of 2θ≈12° and is sharp with high intensity for NiLDH and 0.77NiLDH@0.33YZ. While relatively lower intensity peaks are observed for 0.5NiLDH@0.5YZ and 0.33NiLDH@0.77YZ. The highly intense patterns in a and b planes of NiLDH were gradually suppressed in the hybrids. The XRD pattern of the 0.5NiLDH@0.5YZ hybrid completely matches with that of the corresponding synthesized YZ (Joint committee on powder diffraction standards (JCPDS); 76-110) [Warner, T. E., M. Galsgaard Klokker, and U. G. Nielsen, *Synthesis and Characterization of Zeolite Na—Y and Its Conversion to the Solid Acid Zeolite H—Y. Journal of Chemical Education,* 2017; (94(6): p. 781-785)]. The diffraction peaks of YZ were indexed as per previous report [Zhao, J., et al., *Synthesis and characterization of mesoporous zeolite Y by using block copolymers as templates. Chemical Engineering Journal,* 2016; (284: p. 405-411)]. There were no significant changes in the number of diffraction peaks with respect to YZ except the peak at 2θ=12.3°, 23.4°, 35.3° and 61.9°, which refer to NiLDH peaks, indicating that NiLDH coated inside the YZ pores [Wang, B., et al., *Nickel/USY Catalyst Derived from a Layered Double Hydroxide/Zeolite Hybrid Structure with a High Hydrogenation Efficiency. ChemCatChem,* 2017;

(9(24): p. 4552-4561)]; [Li, R., et al., *Microporous Zeolite@ Vertically Aligned Mg—Al Layered Double Hydroxide Core@ Shell Structures with Improved Hydrophobicity and Toluene Adsorption Capacity under Wet Conditions*. ACS applied materials & interfaces, 2018; (10(41): p. 34834-34839)].

Figure 4:
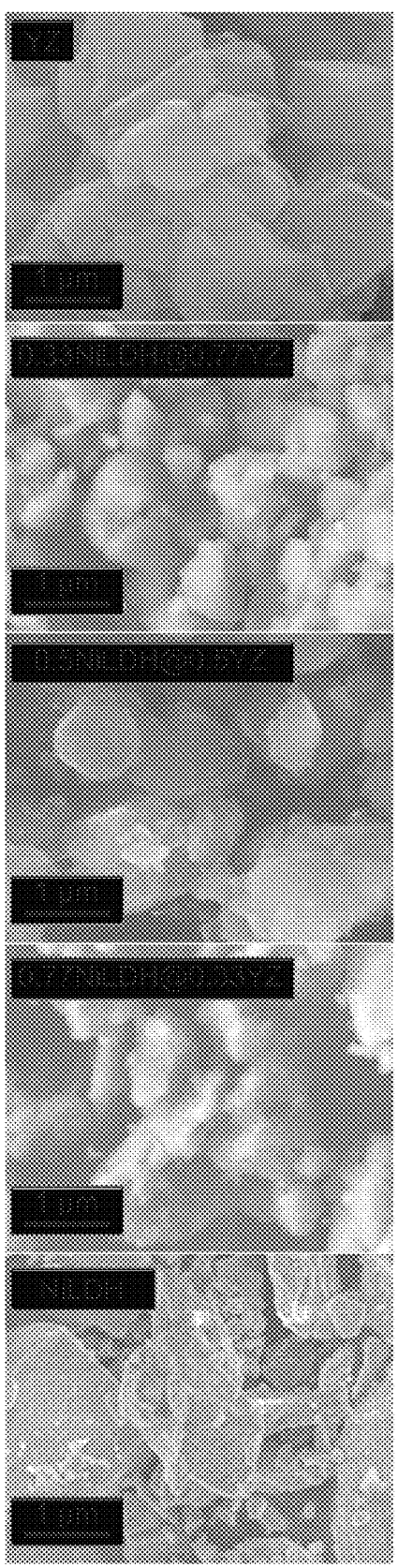
FIG. 4 shows scanning electron microscopy (SEM and EDX) images of NiLDH, YZ and NiLDH, YZ hybrids.
Figure 4:
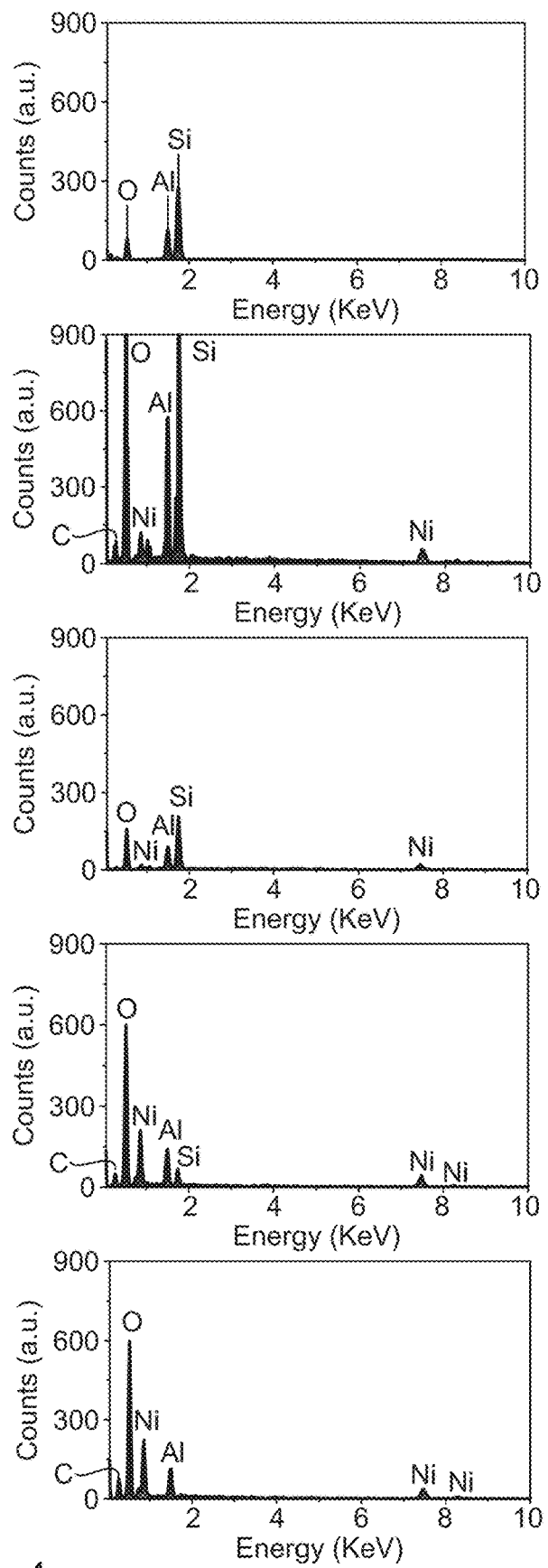

FIG. 4 shows scanning electron microscopy (SEM and EDX) images of NiLDH, YZ and NiLDH, YZ hybrids. The morphology of parent YZ, NiLDH and their hybrids were investigated by scanning electron microscopy. The YZ sample displays a very well-defined and polished shape, while the morphology of the layered NiLDH flakes showed layered double hydroxides structure [Alzhrani, G., et al., *Novel Efficient Pd-Free Ni-Layered Double Hydroxide Catalysts for a Suzuki C—C Coupling Reaction*. ChemistrySelect, 2019; (4(27): p. 7904-7911)]. The intercalation of NiLDH on the Y-zeolite structure is confirmed from SEM images. In 0.33NiLDH@0.77YZ, irregular spots begin to deposit on the outer surface of the zeolite material. The YZ still retained the original form in 0.5NiLDH@0.5YZ with the outer surface roughened from widely dispersed NiLDH, without an aggregation of NiLDH on YZ surface. The degree of dispersion increases monotonically with the increase in NiLDH content, where 0.77NiLDH@0.33YZ showed the maximum roughness of the zeolite surface.

Figure 5:
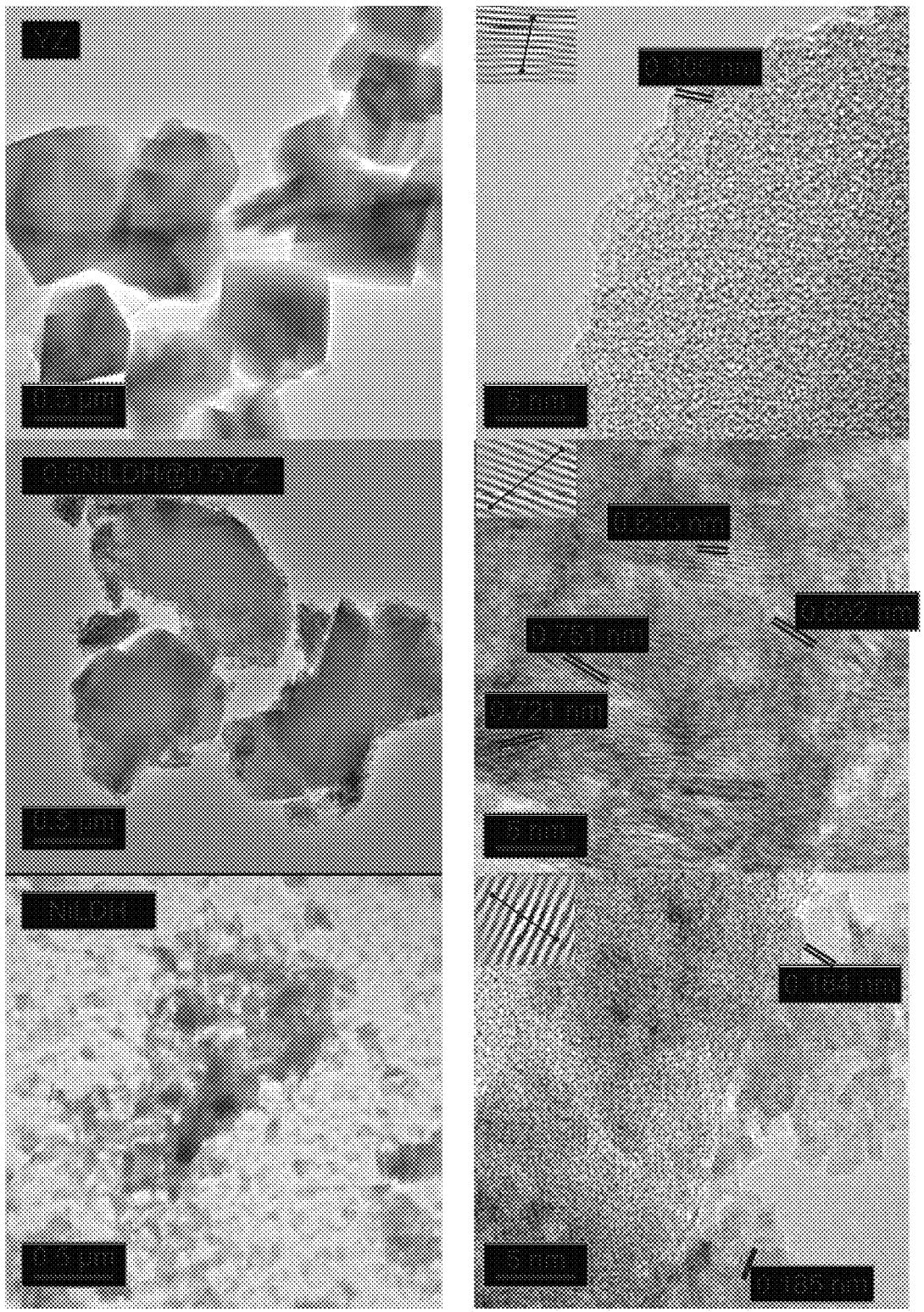
FIG. 5 shows the transmission electron microscopy (TEM) image of YZ with a defined shape with sharp edges.

Referring to FIG. 5, the transmission electron microscopy (TEM) image shows that YZ has a defined shape with sharp edges. The TEM image for 0.5NiLDH@0.5YZ catalyst shows the presence of a significant degree of NiLDH coverage on the surface of the YZ crystallites. The high-resolution transmission electron microscopy (HRTEM) image of 0.5NiLDH@0.5YZ shows a non-uniform lattice fringe compared to YZ, confirming the existence of NiLDH on the YZ surface. In addition, the width of the adjacent lattice fringe is about 0.751 nm which is similar to $d_{003}$ spacing of the NiLDH phase (0.727 nm) [Wang, B., et al., *Nickel/USY Catalyst Derived from a Layered Double Hydroxide/Zeolite Hybrid Structure with a High Hydrogenation Efficiency*. ChemCatChem, 2017; (9(24): p. 4552-4561)]. NiLDH sample shows extra d-spacing at 0.185 nm, which is specific to the layered material.

Figure 6:
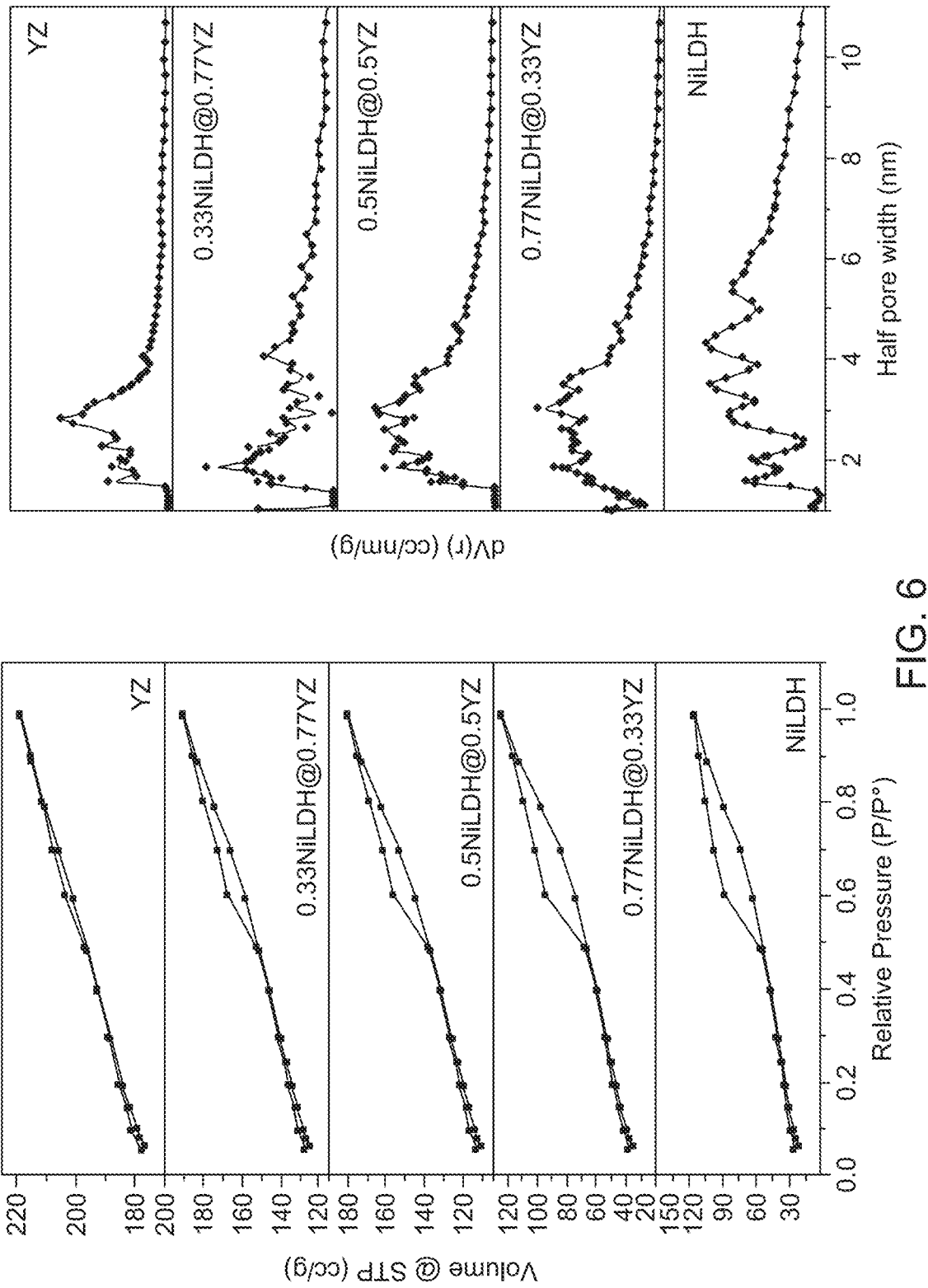
FIG. 6 shows N2 adsorption-desorption isotherms and pore size distribution curves of NiLDH, YZ and NiLDH, YZ hybrids.

FIG. 6 shows N2 adsorption-desorption isotherms and pore size distribution curves of NiLDH, YZ and NiLDH, YZ hybrids. Nitrogen adsorption-desorption for a series of NiLDH@YZ hybrid samples was examined to estimate their specific surface area and porosity. According to IUPAC classification [Thommes, M., et al., *Physisorption of gases, with special reference to the evaluation of surface area and pore size distribution (IUPAC Technical Report)*. Pure and Applied Chemistry, 2015; (87(9-10): p. 1051-10690], all samples show type IV isotherm except YZ that exhibits typical type I isotherm. The H4-type hysteresis loop indicates the presence of mesoporous slit like shape [Kruk, M. and M. Jaroniec, *Gas Adsorption Characterization of Ordered Organic-Inorganic Nanocomposite Materials*. Chemistry of Materials, 2001; (13(10): p. 3169-3183)]. Textural properties for NiLDH, YZ and NiLDHs@YZ hybrids have been summarized in Table-1. The pore size distribution analysis, using density-functional theory (DFT) method, displayed that all the samples have bimodal distribution curves in the microporous and mesoporous ranges. The pore size of YZ was decreased after coating process from 2.8 to 1.1 nm in 0.5NiLDH@0.5YZ hybrid (Table 1). Similar phenomenon was reported when different metals were introduced on porous materials [Tahir, M. and N. S. Amin, *Photocatalytic reduction of carbon dioxide with water vapors over montmorillonite modified $TiO_2$ nanocomposites*. Applied Catalysis B: Environmental, 2013; (142: p. 512-522)]; [Hajimirzaee, S., et al., *Dehydration of methanol to light olefins upon zeolite/alumina catalysts: Effect of reaction conditions, catalyst support and zeolite modification*. Chemical engineering research and design, 2015; (93: p. 541-553)]. The decrease in pore size of the 0.5NiLDH@0.5YZ catalyst compared to the original YZ is due to NiLDH layers blocking the pores during the process of Y-zeolite surface coating. Both Brunauer-Emmett-Teller (BET) and micropore surface areas decreased with NiLDH addition, while the opposite occurred in mesoporous areas. YZ showed the highest BET surface area and micropore area values and pure NiLDH sample showed the opposite values. The micropore volume of YZ decreased while the mesopore volume increased after addition of NiLDH in the hybrid materials. The pronounced decrease in micropore volume in YZ after the coating process is due to the coating of pores by NiLDH particles [Perez-Verdejo, A., et al., *Nanoporous composites prepared by a combination of SBA-15 with Mg Al mixed oxides. Water vapor sorption properties*. Beilstein journal of nanotechnology, 2014; (5(1): p. 1226-1234)]. The calculated hierarchy factor recorded 0.12 for 0.5NiLDH@0.5YZ hybrid catalyst which is double to the value of YZ (0.06) and NiLDH (0.06) samples individually. The suitable hierarchy factor leads to the creation of shorter diffusion path lengths and lower diffusion resistance in this particular catalyst. In addition, the sustainable number of mesopores resist the formation of coke [Xu, S., et al., *Effect of hierarchical ZSM-5 zeolite crystal size on diffusion and catalytic performance of n-heptane cracking*. Frontiers of Chemical Science and Engineering, 2018; (12(4): p. 780-789)].

TABLE 1

The textural properties of YZ, NiLDH and their hybrids.

|  | $S_{BET}^{1}$ (m²/g) | $S_{micro}^{2}$ (m²/g) | $S_{meso}^{3}$ (m²/g) | $V_{total}^{4}$ (cc/g) | $V_{micro}^{5}$ (cc/g) | $V_{meso}^{6}$ (cc/g) | Pore Size Distribution (nm) | HF[7] |
|---|---|---|---|---|---|---|---|---|
| YZ* | 564.4 | 517.7 | 39.8 | 0.34 | 0.27 | 0.06 | 2.8 | 0.06 |
| 0.33NiLDH@0.77YZ | 424.2 | 347.4 | 71.6 | 0.29 | 0.18 | 0.11 | 1.9 | 0.10 |
| 0.5NiLDH@0.5YZ | 379.3 | 297.2 | 79.7 | 0.28 | 0.16 | 0.12 | 1.1 | 0.12 |
| 0.77NiLDH@0.33YZ | 164.0 | 60.9 | 105.2 | 0.19 | 0.03 | 0.15 | 3.0 | 0.11 |
| NiLDH | 124.7 | 12.8 | 126.4 | 0.18 | 0.01 | 0.17 | 4.3 | 0.06 |

*[1]Surface area from BET isotherm ≈ $S_{meso}$ + $S_{micro}$;
[2]Micropore area (From t-plot method);
[3]Mesopore area (From BJH method);
[4]Total pore volume = $V_{meso}$ + $V_{micro}$;
[5]Micropore volume (From t-plot method);
[6]Mesopore volume (From t-plot method);
[7]Hierarchy factor = ($V_{micro}/V_{total}$) × ($S_{meso}/S_{BET}$)

Figure 7:
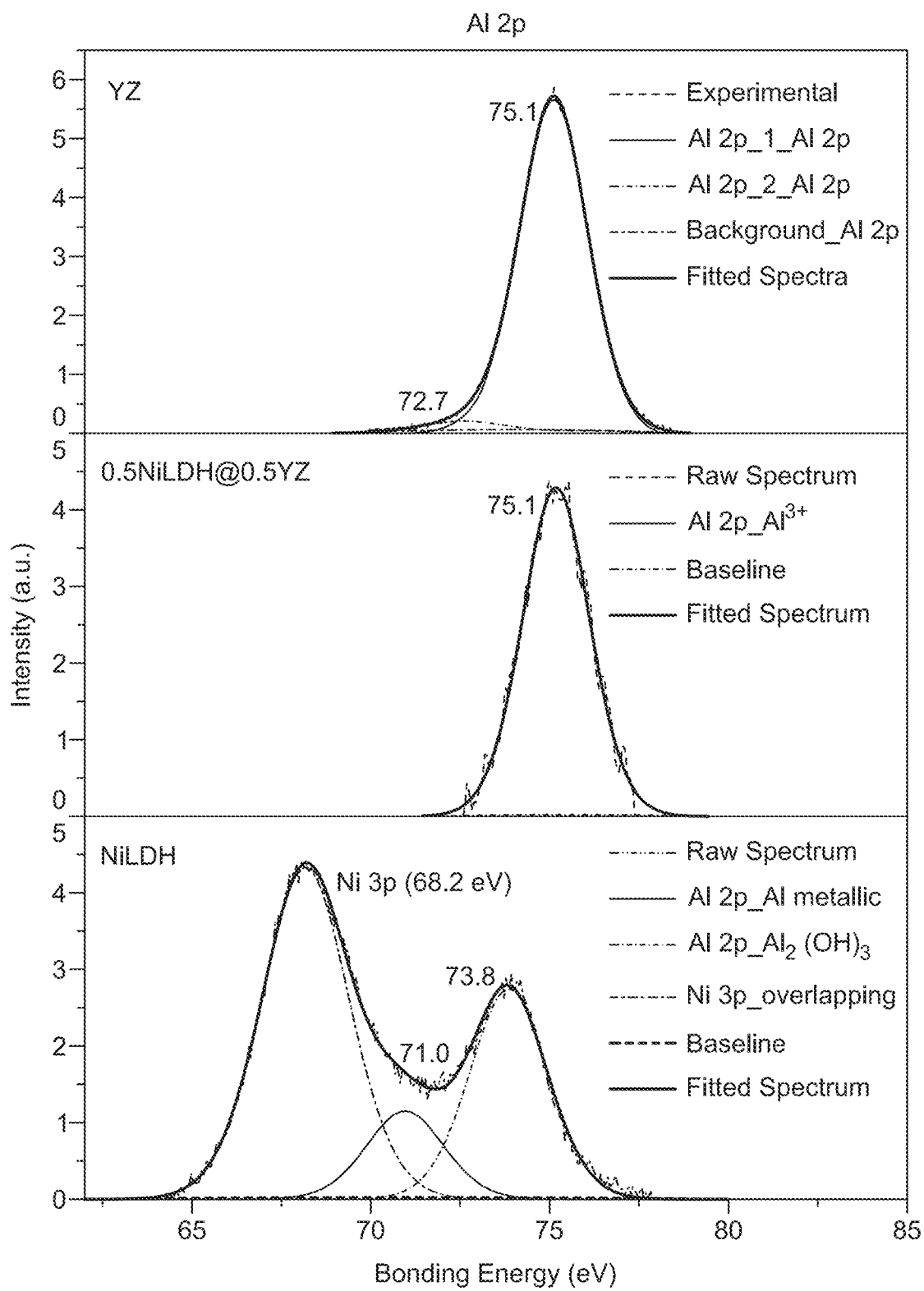
FIG. 7 shows the deconvoluted X-ray photoelectron microscopy (XPS) spectrum of the catalysts.
Figure 7:
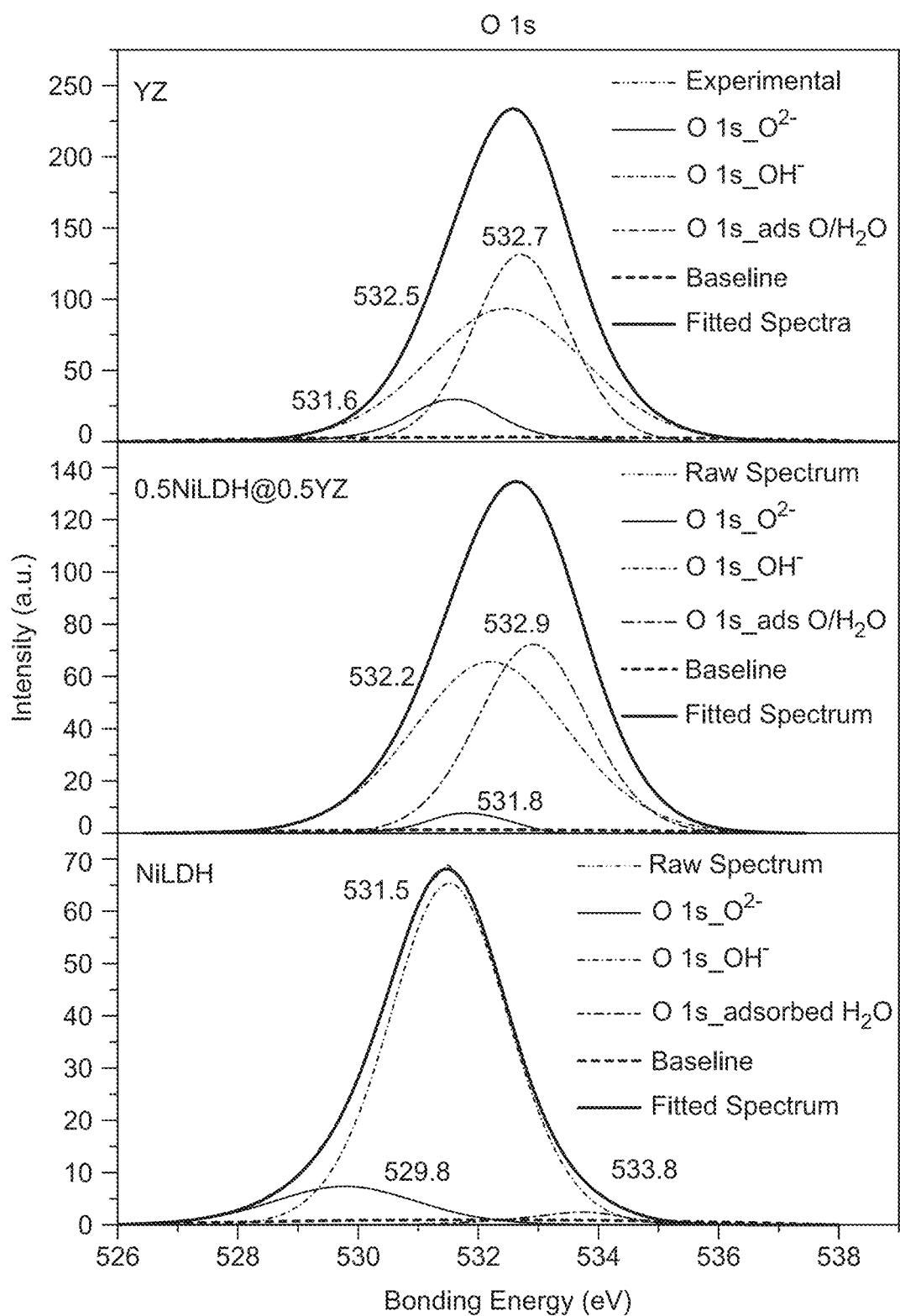
Figure 7:
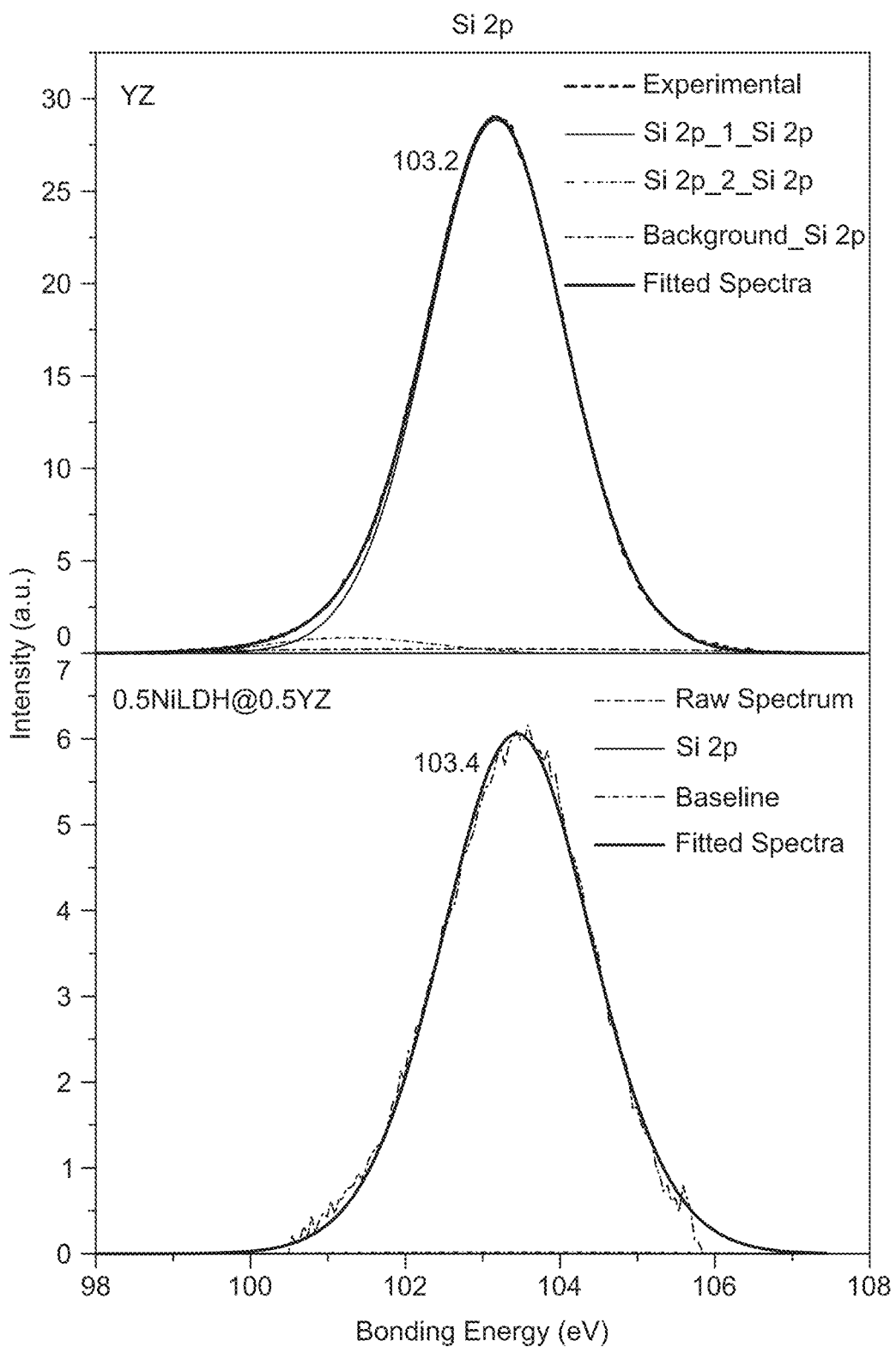
Figure 7:
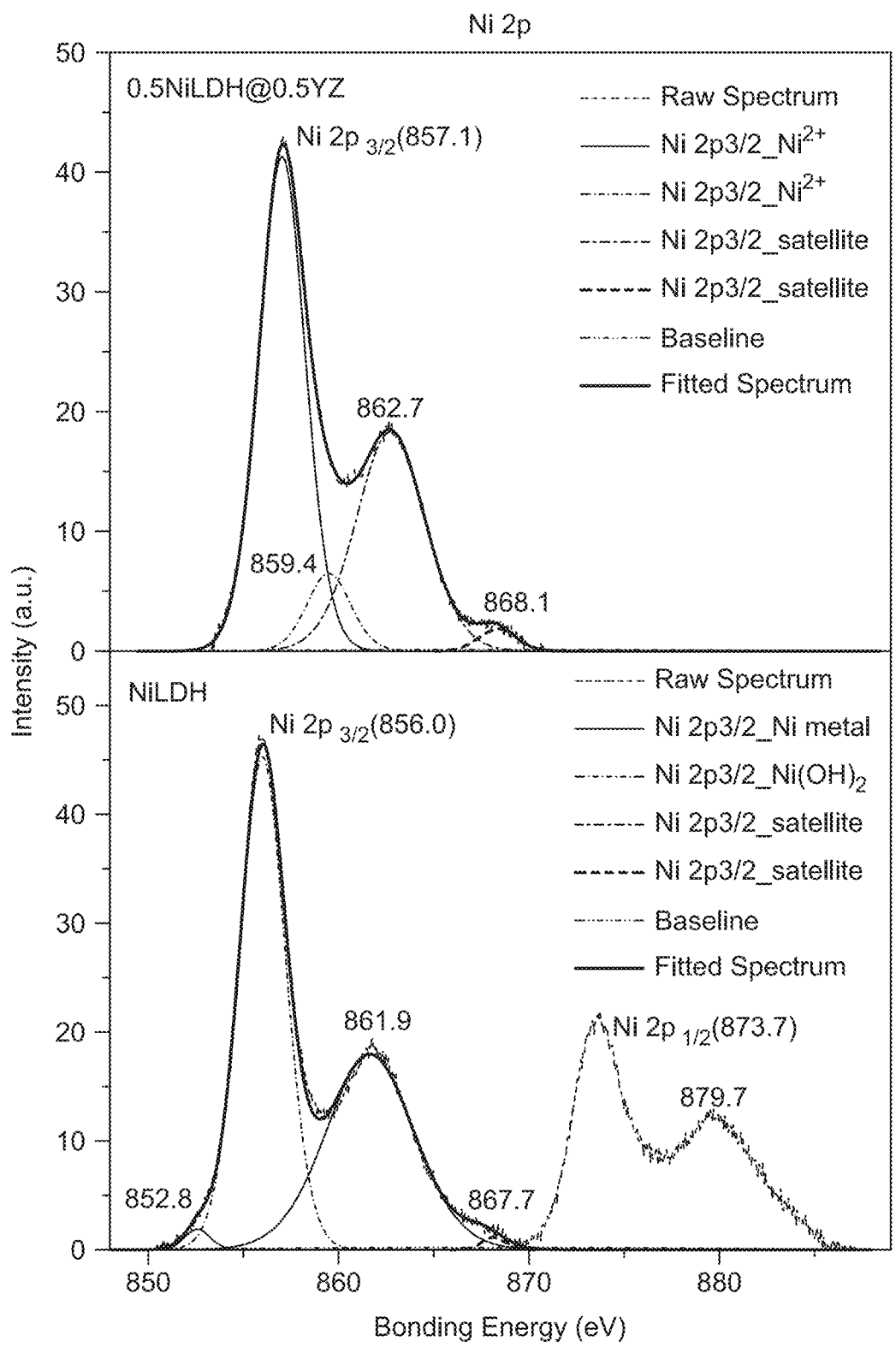

FIG. 7 depicts the deconvoluted X-ray photoelectron microscopy (XPS) spectrum of the catalysts. The analysis shows the surface structure and provides details about the presence of Ni, Al, O and Si within the surface of catalysts along with the oxidation state of the metals. An envelope for the Al 2p band at 75.1 eV in YZ sample and 0.5NiLDH@0.5YZ hybrid is illustrated and this shows the presence of $Al^{3+}$ ion that gets bonded to oxygen and silicon (Al—O—Si) in zeolite structure [Borade, R. B. and A. Clearfield, *Characterization of acid sites in Beta and ZSM-20 zeolites. The Journal of Physical Chemistry*, 1992; (96 (16): p. 6729-6737)]. The binding energy of Al 2p in pure NiLDH sample resulted in a peak at 73.8 eV, while the peak that appeared at 68.2 eV contributed to Ni 3p [El Gabaly, F., et al., *Oxidation stages of Ni electrodes in solid oxide fuel cell environments. Physical Chemistry Chemical Physics*, 2013; (15(21): p. 8334-8341)]. The deconvoluted Al 2p peaks at 73.8 eV indicates the presence of $Al^{3+}$ bonded to hydroxide layers (Al—OH) [Deng, L., et al., *Hierarchically magnetic Ni—Al binary layered double hydroxides: towards tunable dual electro/magneto-stimuli performances. Journal of industrial and engineering chemistry*, 2018; (58: p. 163-171)].

FIG. 7 displays the deconvoluted XPS band of is of O in YZ, 0.5NiLDH@0.5YZ and NiLDH samples and that show the presence of isolated oxygen ($O^{2-}$), the lattice oxygen ($OH^-$) and oxygen from the adsorbed water. The figure shows that the peak intensity of 2p of Si in YZ and 0.5NiLDH@0.5YZ, which is reduced after coating with NiLDH indicating that the Si content on the surface decreased significantly [Wang, B., et al., *Nickel/USY Catalyst Derived from a Layered Double Hydroxide/Zeolite Hybrid Structure with a High Hydrogenation Efficiency. ChemCatChem*, 2017; (9(24): p. 4552-4561)]. Also, NiLDH spectrum shows the two obvious shakeup satellites at 856.0 and 873.7 eV which can be identified as signals for 2p3/2 of Si and 2p1/2 of $Ni^{2+}$, respectively. These satellite lines are the fingerprints of $Ni^{2+}$ ions in an environment of oxide ions ($O^{2-}$) [Abelian, G., et al., *Self-assembly of 1D/2D hybrid nanostructures consisting of a Cd (II) coordination polymer and NiAl-layered double hydroxides. Polymers*, 2016; (8(1): p. 5)]. In XPS spectrum of 0.5NiLDH@0.5YZ hybrid, the Ni 2p3/2 peak shifted to higher binding energy from 856.0 eV to 857.1 eV. The position of Ni 2p peak is influenced by the local chemical or physical environment around Ni species besides the formal oxidation state. The Ni 2p peak shifts to higher binding energy when the charge density around it decreases. The existence of the acidic sites of YZ (Al and Si) around the Ni species leads to a decrease in the charge density around Ni and the slight increase in binding energy [Metin, Ö. and S. Özkar, *Synthesis and characterization of poly (N-vinyl-2-pyrrolidone)-stabilized water-soluble nickel (0) nanoclusters as catalyst for hydrogen generation from the hydrolysis of sodium borohydride. Journal of Molecular Catalysis A: Chemical*, 2008; (295(1-2): p. 39-46)]; [Oliver-Tolentino, M. A., et al., *An approach to understanding the electrocatalytic activity enhancement by superexchange interaction toward OER in alkaline media of Ni—Fe LDH. The Journal of Physical Chemistry C*, 2014; (118(39): p. 22432-22438)].

Figure 8:
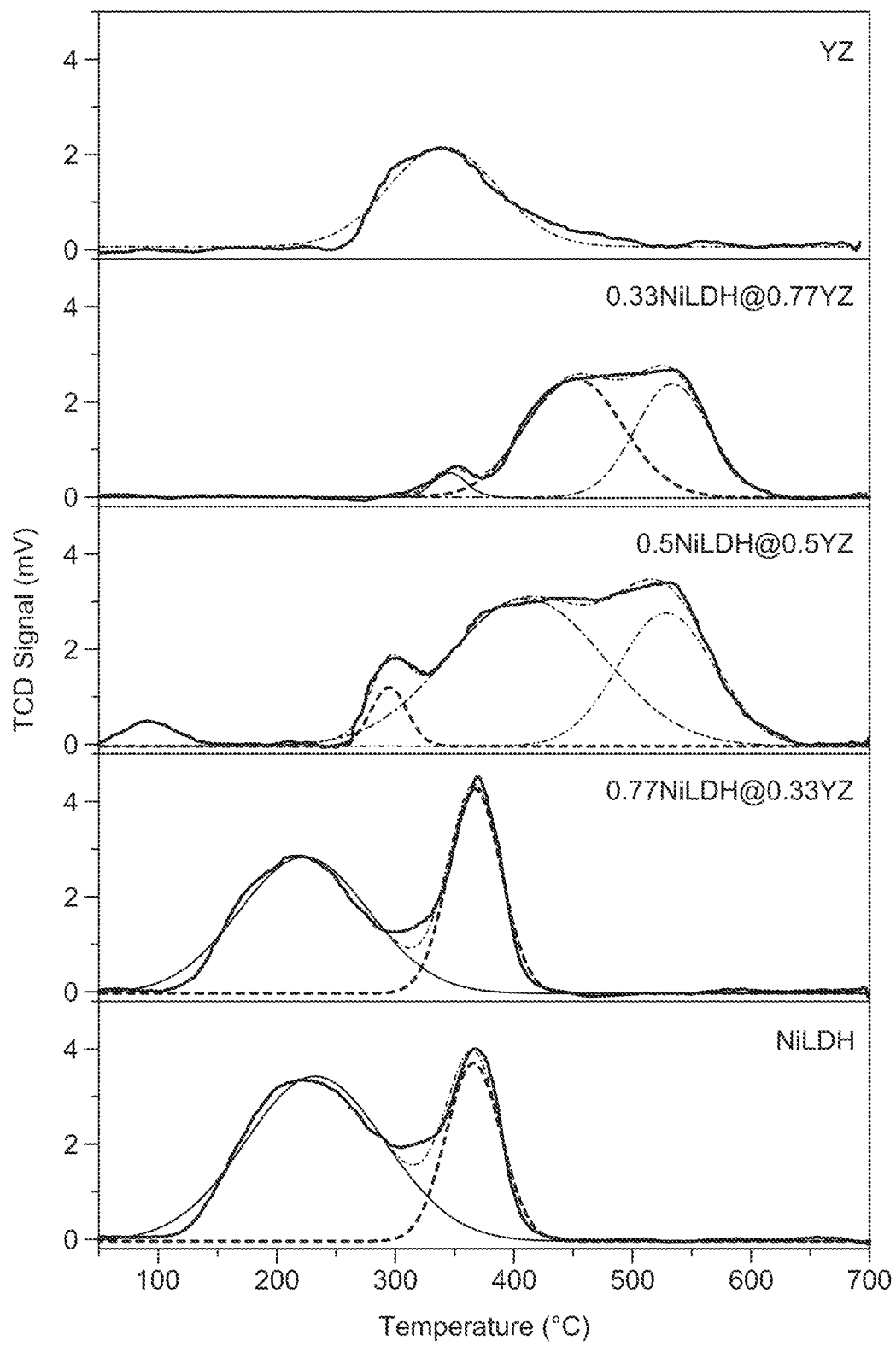
FIG. 8 shows temperature-programmed desorption (TPD-$CO_2$) profile for NiLDH, YZ and NiLDH, YZ hybrids.

FIG. 8 shows temperature-programmed desorption (TPD-$CO_2$) profile for NiLDH, YZ and NiLDH, YZ hybrids. The basicity of the different catalysts was determined by temperature-programmed desorption (TPD-$CO_2$) because the types of basic sites are detectable by $CO_2$ adsorption. The chemisorbed peaks are compared according to the temperatures at which the peaks are shown. Bicarbonate and bidentate species decompose at low and moderate temperatures (−100-420° C.) and traced to relevant peaks. The peak that decomposed at higher temperature (≈540° C.) is due to the presence of monodentate species [Diez, V., C. Apesteguia, and J. Di Cosimo, *Effect of the chemical composition on the catalytic performance of MgyAlOx catalysts for alcohol elimination reactions. Journal of Catalysis*, 2003; (215(2): p. 220-233)]; [Ewald, S. and O. Hinrichsen, *On the interaction of CO2 with Ni—Al catalysts. Applied Catalysis A: General*, 2019; (580: p. 71-80)]. FIG. 8 shows that each of the hybrids have different types of basic sites, whereas TPD-$CO_2$ profile of YZ catalyst shows just one peak at 340° C. The TPD-$CO_2$ of 0.77NiLDH@0.33YZ and NiLDH have identical profiles that are distinct from 0.5NiLDH@0.5YZ, which has a unique profile. The TPD-$CO_2$ profile of all hybrids (except 0.33NiLDH@0.77YZ) and NiLDH show peaks within the range of 100-355° C. due to the desorption of weakly bond $CO_2$ and the breakdown of carbonate ions existing in the interlayer of LDH samples. In the TPD-$CO_2$ profiles of 0.5NiLDH@0.5YZ and 0.33NiLDH@0.77YZ, the peaks extend to up to 520° C. and this can be related to tightly bonded species of monodentate or bidentate carbonate. In addition, there is a peak at about 420° C. that is attributed to bicarbonate species bonded to weak or medium basic strength sites [Abelló, S., et al., *Study of alkaline-doping agents on the performance of reconstructed Mg—Al hydrotalcites in aldol condensations. Applied Catalysis A: General*, 2005; (281(1-2): p. 191-198)].

The profiles of TPD-$CO_2$ for all catalysts were integrated to measure the amount of $CO_2$ formed from the subtraction of the corresponding profiles. From Table 2, it is clear that 0.5NiLDH@0.5YZ catalyst has higher total number of basic sites (40.4 µmol/g), which reveals the stronger dispersion of NiLDH in the YZ cavities.

TABLE 2

Results of $NH_3$-TPD and $CO_2$-TPD profiles

| Catalyst | Ni (% w/w) [1] | Total $CO_2$ uptake (µmol/g) | Total acidity (µmol/g) |
|---|---|---|---|
| YZ | — | 9.3 | 277.1 |
| 0.33NiLDH@0.77YZ | 0.6 | 20.9 | 310.2 |
| 0.5NiLDH@0.5YZ | 0.7 | 40.4 | 549.1 |
| 0.77NiLDH@0.33YZ | 0.8 | 24.4 | 269.4 |
| NiLDH | 0.81 | 29.4 | 256.8 |

*[1] From ICP analysis.

Figure 9:
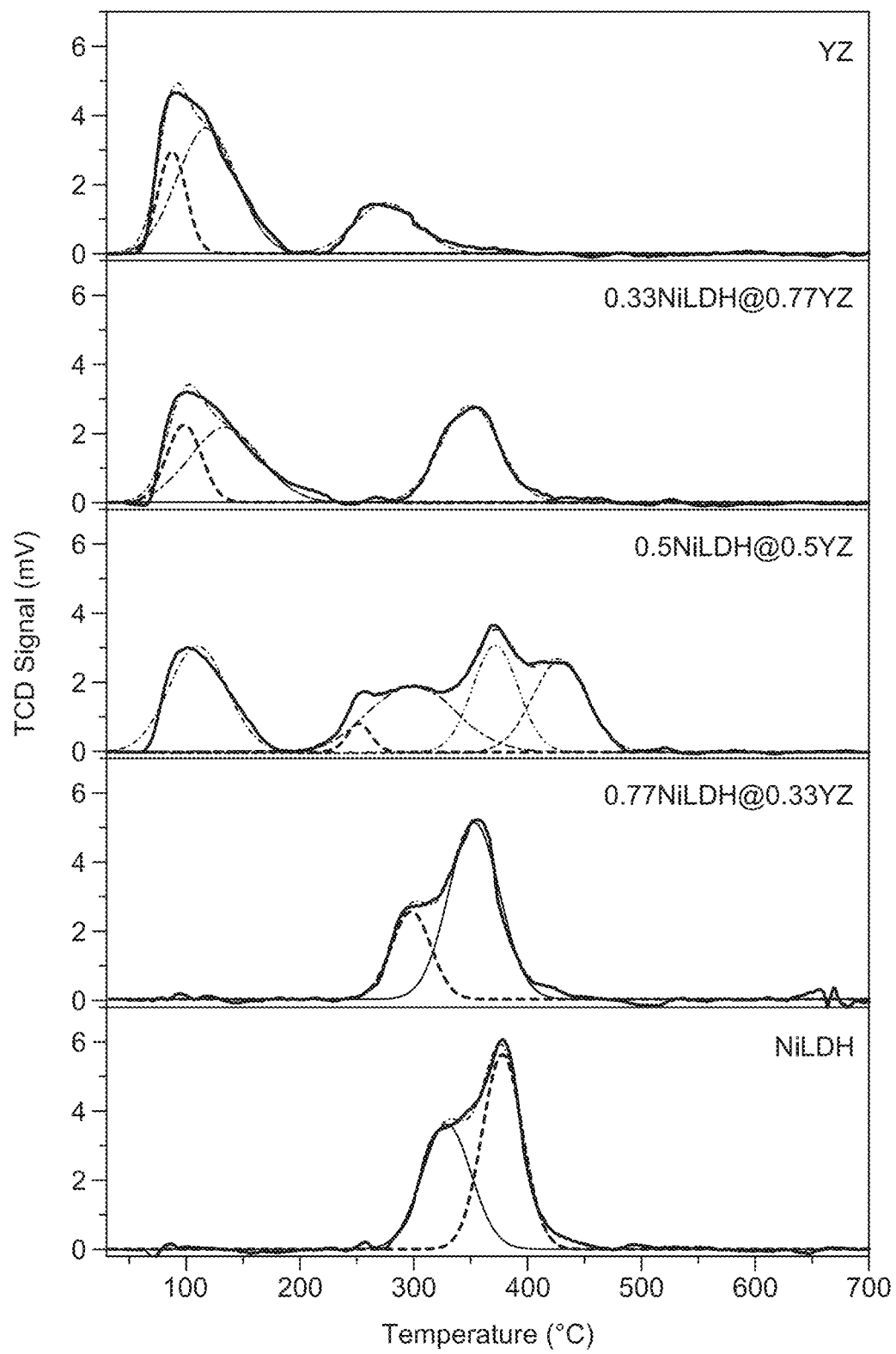
FIG. 9 show the acidity of the catalysts studied by temperature-programmed desorption (TPD-NH3) profiles.

FIG. 9 depicts the acidity of the catalysts studied by temperature-programmed desorption (TPD-NH3) profiles. The overall acidity of the catalysts is measured from the amount of ammonia desorbed at different temperatures. The strength and number of acidic surface centers are estimated from the maximum temperature intensity and location, respectively. Ammonia desorption profile of the catalysts is divided into three regions namely (1) weak (100-250° C.), (2) medium (250-400° C.) and (3) strong (400-700° C.) acid strengths [Condon, J. B., *Surface Area and Porosity Determinations by Physisorption: Measurement, Classical Theories and Quantum Theory*. 2019; (Elsevier)]. The NiLDH exhibited two peaks at 329° C. and 378° C. which are under medium temperature range corresponding to moderate acid sites.

The TPD-NH3 profile of 0.77NiLDH@0.33YZ catalyst is similar to NiLDH, but the maximum temperature and peak intensities are lesser in 0.77NiLDH@0.33YZ than NiLDH due to lesser acidity. YZ catalyst also has two different peaks at lower maximum temperatures (107° C. and 274° C.) showing both weak and moderate acid sites. The TPD-NH3 profile of 0.33NiLDH@0.77YZ also shows two different peaks corresponding to poor and moderate acid sites at higher temperatures (117 and 350° C.) relative to YZ. The TPD-NH3 profile of 0.5NiLDH@0.5YZ exhibited five peaks at different temperatures such as 110° C. (weak acid site), 252° C., 299° C., 372° C. (moderate acid sites) and at 428° C. (strong acid sites) as depicted in FIG. 9.

Figure 10:
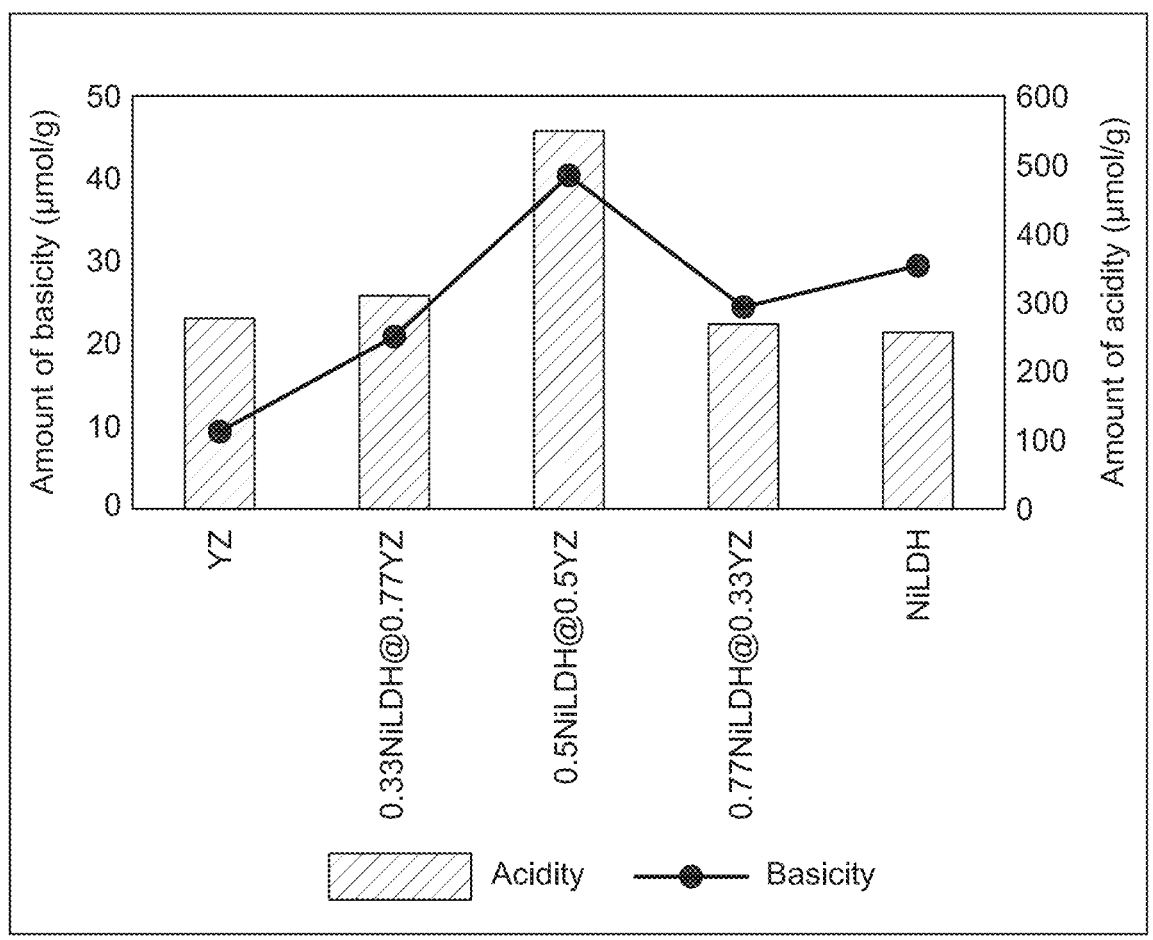
FIG. 10 shows the acidic-basic features of various catalyst derived from $NH_3$-TPD and $CO_2$-TPD profile analysis.

Referring to FIG. 10, the acidic-basic features of various catalyst derived from NH3-TPD and $CO_2$-TPD profile analysis are displayed. The 0.5NiLDH@0.5YZ hybrid reveals the highest acid-base bifunctional feature relative to all the investigated catalysts. Higher acid-base bifunctional feature of catalysts at one provides the surface to interact with organic molecules and also results in it being the site for C—C coupling reactions [Maaten, B., et al., *Cu-modified hydroxy-apatite as catalyst for Glaser-Hay CC homo-coupling reaction of terminal alkynes. Journal of Molecular Catalysis A: Chemical*, 2014; (393: p. 112-116)].

Figure 11:
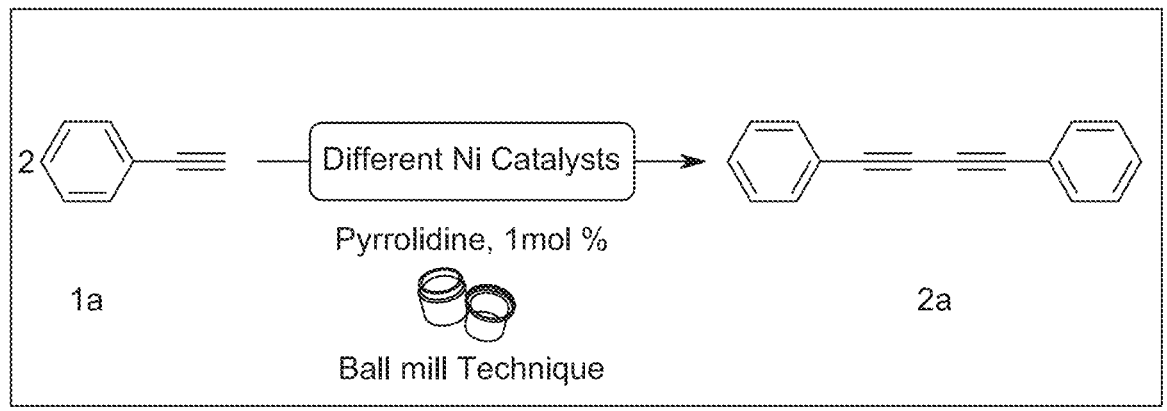
FIG. 11 shows the optimization of catalyst for the Glaser type reaction.

FIG. 11 depicts the optimization of catalyst for the Glaser type reaction. The catalysts prepared are used to develop a protocol for heterogeneous nickel catalyzed Glaser homocoupling reaction under mechanochemical agitation in a ball mill. And further, study the catalytic activities of the prepared NiLDH@YZ catalysts that allowed the transformation of terminal alkyne 1 into the corresponding 1,4-buta-1,3-diynes derivative 2 in a time-efficient as well as energy-efficient manner. At the outset, NiLDH, YZ, 0.77NiLDH@0.33YZ, 0.5NiLDH@0.5YZ and 0.33NiLDH@0.77YZ catalysts were tested for their catalytic activity in ball mill, under solvent free conditions and results were cited in Table 3. These catalysts have the advantages that they have a minimal impact to the environment and can be easily recycled.

Notably, the catalytic materials used in this reaction act as grinding auxiliaries in addition to its role as a catalyst where all the reactants are liquid. It is clear from results depicted in (Table 3) that even after utilizing a ball mill even after 6 h, no desired product 2a was formed in absence of catalyst (Table 3, Entry 1).

TABLE 3

Optimization of reaction conditions (catalyst and time) for homocoupling of terminal alkynes.

| Entry | Catalyst | Time (mm.) | Yield (%) |
|---|---|---|---|
| 1 | Catalyst-free | 360 | 0 |
| 2 | NiLDH | 180 | 10 (trace) |
| 3 | YZ | 180 | 12 (trace) |
| 4 | 0.77NiLDH@0.33YZ | 130 | 61 |
| 5 | 0.5 NiLDH@0.5YZ | 60 | 83 |
| 6 | 0.33NiLDH@0.77YZ | 180 | 23 |

Reaction conditions: catalyst (400 mg), phenylacetylene (2 mmol), pyrrolidine (1 mol %) and ball mill frequency (30 Hz).

Figure 12:
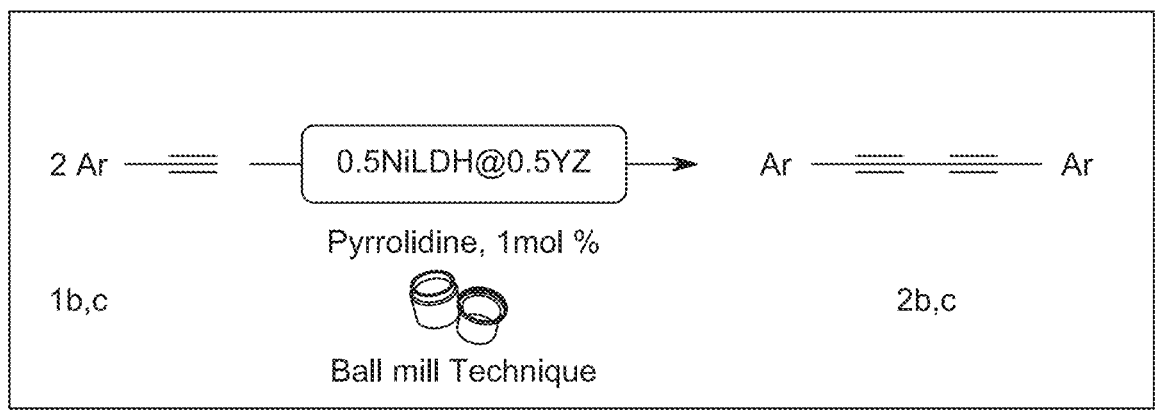
FIG. 12 shows homocoupling of terminal alkyne utilizing 0.5NiLDH@0.5YZ catalyst.

Referring to FIG. 12, homocoupling of terminal alkyne utilizing 0.5NiLDH@0.5YZ catalyst is depicted. The best yield of 83% of the desired product 2 was reached using 0.5NiLDH@0.5YZ catalyst in 60 mins (Table 3, Entry 5). Furthermore, a lower yield with longer period of time (61% at 130 min. and 23% at 180 min.) was observed using 0.77NiLDH@0.33YZ and 0.33NiLDH@0.77YZ catalysts (Table 3, Entry 4 & 6), respectively. It is worth noticing that only trace product was formed using NiLDH and YZ alone (Table 3, Entries 2 & 3). Further, effect of time and frequency of ball mill on catalytic system were examined (Table 4) with same amount of catalyst. The best frequency for this reaction protocol was noted at 30 Hz (Table 4, Entry 3), in which the desired product 2a was isolated in 83% yield and no other product was noticed.

TABLE 4

Optimization of reaction condition (time and ball mill frequency for homocoupling of terminal alkynes.

| Entry | Time (mm.) | Yield (%) | Ball-mill frequency (Hz) |
|---|---|---|---|
| 1 | 120 | 62 | 20 |
| 2 | 90 | 70 | 25 |
| 3 | 60 | 83 | 30 |

Reaction conditions: 0.5NiLDH@0.5YZ catalyst (400 mg), phenylacetylene (2 mmol) and pyrrolidine (1 mol %).

The scope and generality of this protocol was further tested for various derivatives of terminal alkynes (Table 5) using 0.5NiLDH@0.5YZ catalyst under the optimized conditions.

TABLE 5

Scope of homocoupling under optimized conditions.

| Entry | Product | Time (mm.) | Yield (%) |
|---|---|---|---|
| 1 | 2a | 60 | 83 |
| 2 | 2b | 0 | 85 |
| 3 | 2c | 60 | 81 |

Reaction conditions: 0.5NiLDH@0.5YZ catalyst (400 mg), phenylacetylene (2 mmol) and pyrrolidine (1 mol %).

All the products were well characterized using nuclear magnetic resonance (NMR) spectral data. In the 1H NMR spectra, disappearance of singlet peak of acetylenic hydrogen confirms the formation of desired coupled products (2a-c). The spectral data of the compounds 2a-c are listed below:

1,4-Diphenylbuta-1,3-diyne (2 a): $^1$H NMR (400 MHz, CDCl$_3$): δ=7.49-7.61 (m, 4H), 7.43-7.48 (m, 6H). $^{13}$C NMR (100 MHz, CDCl$_3$): δ=132.8, 130.5, 129.4, 120.8, 82.3, 73.9.

1,4-Bis(p-tolyl)buta-1,3-diyne (2 b): $^1$H NMR (400 MHz, CDCl$_3$): δ=7.39 (d, J=8.0 Hz, 4H), 7.12 (d, J=8.0 Hz, 4H), 2.34 (s, 6H). $^{13}$C NMR (100 MHz, CDCl$_3$): δ=135.9, 130.5, 129.4, 120.1, 83.2, 75.3, 74.5, 27.1.

1,4-Bis(p-methoxyphenyl)buta-1,3-diyne (2 c): $^1$H NMR (400 MHz, CDCl$_3$): δ=7.44 (d, J=8.8 Hz, 4H), 6.83 (d, J=8.8 Hz, 4H), 3.80 (s, 6H). $^{13}$C NMR (100 MHz, CDCl$_3$): δ=160.1, 133.9, 114.0, 113.8, 81.1, 72.8, 55.2.

1,4-Bis(p-methoxyphenyl)buta-1,3-diyne (2 c): $^1$H NMR (400 MHz, CDCl$_3$): δ=7.44 (d, J=8.8 Hz, 4H), 6.83 (d, J=8.8 Hz, 4H), 3.80 (s, 6H). $^{13}$C NMR (100 MHz, CDCl$_3$): δ=160.1, 133.9, 114.0, 113.8, 81.1, 72.8, 55.2.

Reusability of 0.5NiLDH@0.5YZ Catalyst

Figure 13:
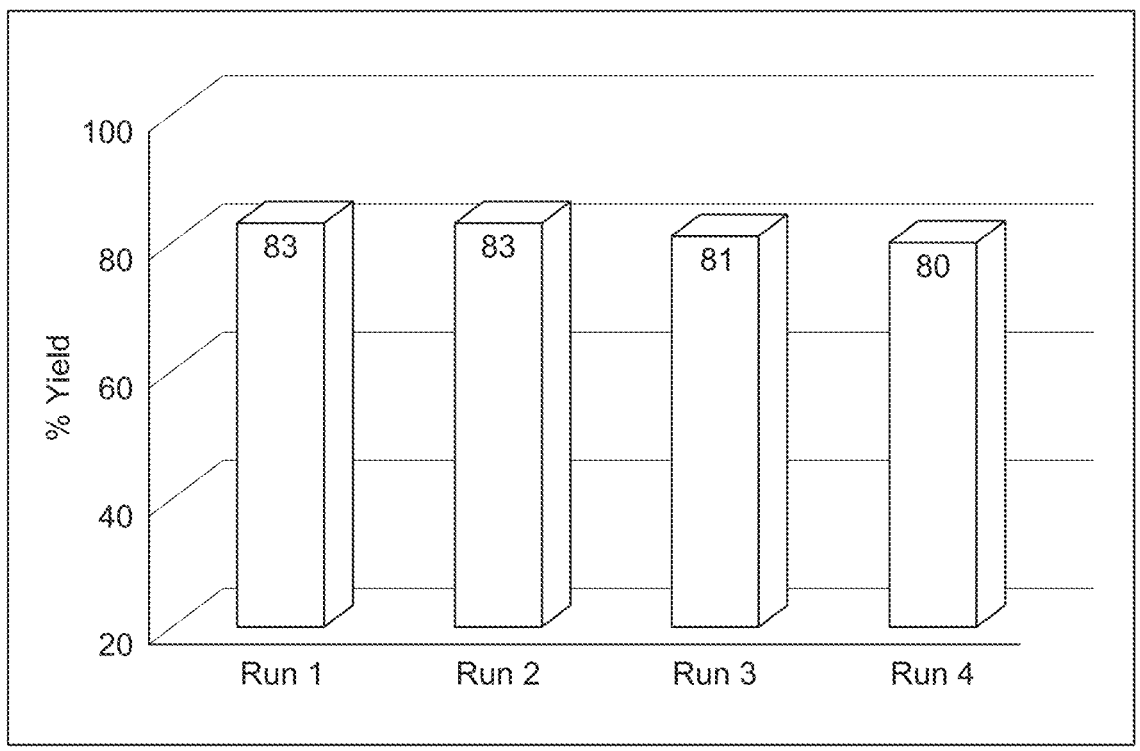
FIG. 13 shows results of recyclability of 0.5NiLDH@0.5YZ catalyst under optimized reaction conditions.

Referring to FIG. 13, results of recyclability of 0.5NiLDH@0.5YZ catalyst under optimized reaction conditions are shown. The reusability of the 0.5NiLDH@0.5YZ catalyst was tested for several reaction cycles under optimized reaction conditions, the catalyst removed after filtration, washed with hot ethyl acetate and dried under vacuum. The recovered catalyst was used under the same reaction conditions four times. FIG. 13 shows that the regenerated catalyst conducts the reaction efficiently under the same conditions even after a four-fold use.

Figure 14:
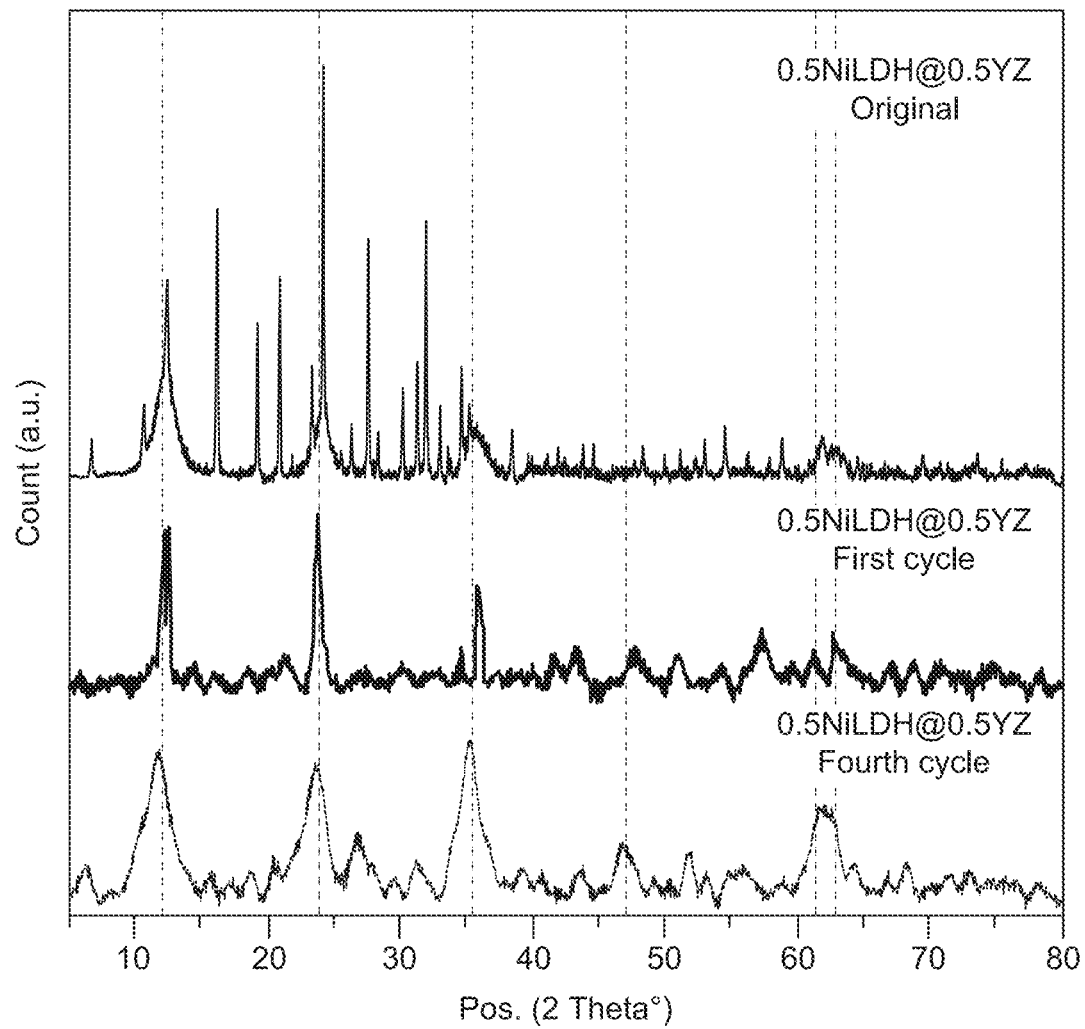
FIG. 14 shows XRD of used 0.5NiLDH@0.5YZ catalysts after first and fourth cycles.

FIG. 14 shows XRD of used 0.5NiLDH@0.5YZ catalysts after first and fourth cycles. A slight decay in the catalytic activity of the 0.5NiLDH@0.5YZ catalyst was observed in third and fourth cycles which was studied by comparing XRD of the original catalyst with the corresponding regenerated catalyst after first and last cycle of Glaser reaction. XRD analysis shows regenerated catalysts losing crystallinity under mechanochemical force while maintaining their layered structure. It is clear from FIG. 14 that the intensity of diffraction peaks that originated from Y-zeolite clearly decreased due to the breakup of Si—O—Si and Si—O—Al bonds as reported by previous studies [Kurniawan, T., et al., *Mechanochemical route and recrystallization strategy to fabricate mordenite nanoparticles from natural zeolites. Crystal Growth & Design,* 2017; (17(6): p. 3313-3320]; [Kadja, G. T., et al., *Sequential mechanochemical and recrystallization methods for synthesizing hierarchically porous ZSM-5 zeolites. Microporous and Mesoporous Materials,* 2020; (308: p. 110550)]; [Kosanovic, C., et al., *Study of structural transformations in potassium-exchanged zeolite A induced by thermal and mechanochemical treatments. Journal of materials science,* 1997; (32(1): p. 73-78]; [Inagaki, S., et al., *Improvement in the catalytic properties of ZSM-5 zeolite nanoparticles via mechanochemical and chemical modifications. Catalysis Science & Technology,* 2016; (6(8): p. 2598-2604)]. Although peaks due to NiLDH showed to be distinctly resistant to mechanical force of ball milling, the intensities of its distinguished XRD peaks in regenerated catalysts are significantly decreased [Szabados, M., et al., *Structural reconstruction of mechanochemically disordered CaFe-layered double hydroxide. Applied Clay Science,* 2019; (174: p. 138-145)]; [Wang, Y., et al., *Structural and textural evolution of nanocrystalline Mg Al layered double hydroxides during mechanical treatment. Applied clay science,* 2013; (80: p. 334-339)]. XRD pattern of regenerated catalyst after the first cycle showed marked peak broadening that became wider after the last cycle, due to reduction of crystallinity and deformation of particle size induced by the milling action. The crystallite size was calculated for the original and regenerated catalysts (after first and last cycles) to demonstrate the degree of deformation of layered structure, which was found as 53.6, 16.5 and 5 nm, respectively but layered structure was retained even after the last cycle. The slightly decay in catalytic activity of 0.5NiLDH@0.5YZ is due to weight loss during the workup process, deformation in regenerated catalysts and surface defects.

The methods of the present disclosure show several advantages for performing a terminal alkyne dehydrogenation coupling reaction using the transitional metal LDH@Y-zeolite hybrid catalyst along with the ball milling technique. One advantage of the embodiments according to the present disclosure is rapid and efficient reaction. Another advantage of the method of the present disclosure is the reaction occurs in solvent free conditions and have the advantages that hybrid catalyst has a minimal impact to the environment, and the hybrid catalyst can be easily recycled. Yet another advantage of the embodiments of the present disclosure is that the methods are fast, robust, reproducible, sensitive, and cost effective. An important advantage of the methods of the present disclosure is the methods are simple one pot synthesis type methods and provide an advantage over complex methods used currently.

It is understood that the examples, embodiments and teachings presented in this application are described merely for illustrative purposes. Any variations or modifications thereof are to be included within the scope of the present application as discussed.

What is claimed is:

1. A method for performing a terminal alkyne dehydrogenation coupling reaction, the method comprising:
   combining a transitional metal LDH@Y-zeolite hybrid catalyst, to a terminal alkyne, and pyrrolidine to form a mixture;
   transferring a portion of the mixture into a ball mill;
   performing a mechanochemical agitation of the portion of the mixture in the ball mill for a first predetermined time to form a reaction mixture;
   oxidizing the reaction mixture for a second predetermined time;
   filtering the oxidized reaction mixture to obtain a filtrate;
   concentrating the filtrate in a vacuum under reduced pressure; and
   purifying the concentrated filtrate using chromatography to obtain a purified end product of the terminal alkyne dehydrogenation coupling reaction.

2. The method of claim 1, further comprising filtering the oxidized reaction mixture using ethyl acetate.

3. The method of claim 1, wherein a yield of the purified end product is more than or equal to 80%.

4. The method of claim 1, wherein the reaction is a solvent-free reaction.

5. The method of claim 1, further comprising using the transitional metal LDH@Y-zeolite hybrid catalyst for at least 4 cycles.

6. The method of claim 1, further comprising, oxidizing the reaction mixture using an oxidant, wherein the oxidant is air.

7. The method of claim 1, wherein the coupling reaction is completed in less than or equal to 60 minutes.

8. The method of claim 1, further comprising sonicating the reaction mixture for less than or equal to 5 minutes.

9. The method of claim 1, wherein the coupling reaction is a homocoupling reaction.

10. The method of claim 9, wherein the homocoupling reaction is a Glaser homocoupling.

11. The method of claim 1, where the coupling reaction is a cross-coupling reaction.

12. The method of claim 1, wherein the transitional metal LDH@Y-zeolite hybrid catalyst is a NiLDH@YZ hybrid catalyst.

13. The method of claim 12, wherein the NiLDH@YZ hybrid catalyst is a 0.5NiLDH@0.5YZ hybrid catalyst.

* * * * *